(12) United States Patent
Yan et al.

(10) Patent No.: US 9,999,630 B2
(45) Date of Patent: *Jun. 19, 2018

(54) TRADITIONAL CHINESE MEDICINE COMPOSITION, AND PREPARATION AND APPLICATION THEREOF

(71) Applicant: TASLY PHARMACEUTICAL GROUP CO., LTD, Tianjin (CN)

(72) Inventors: Xijun Yan, Tianjin (CN); Naifeng Wu, Tianjin (CN); Kaijing Yan, Tianjin (CN); Zhengliang Ye, Tianjin (CN); Shunnan Zhang, Tianjin (CN); Lihong Zhou, Tianjin (CN); Wensheng Zhang, Tianjin (CN); Hai'ou Dong, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 79 days.

This patent is subject to a terminal disclaimer.

(21) Appl. No.: 14/903,995

(22) PCT Filed: Jul. 11, 2014

(86) PCT No.: PCT/CN2014/082102
§ 371 (c)(1),
(2) Date: Jan. 8, 2016

(87) PCT Pub. No.: WO2015/003659
PCT Pub. Date: Jan. 15, 2015

(65) Prior Publication Data
US 2016/0175336 A1    Jun. 23, 2016
US 2017/0157156 A9    Jun. 8, 2017

(30) Foreign Application Priority Data

Jul. 11, 2013 (CN) .......................... 2013 1 0290968
Aug. 29, 2013 (CN) .......................... 2013 1 0384234
Jan. 30, 2014 (CN) .......................... 2014 1 0044675
Mar. 10, 2014 (CN) .......................... 2014 1 0085152

(51) Int. Cl.
*A61K 36/00* (2006.01)
*A61K 31/704* (2006.01)
*A61K 36/537* (2006.01)
*A61K 36/258* (2006.01)
*A61K 31/045* (2006.01)
*A61K 9/20* (2006.01)
*A61K 31/192* (2006.01)
*A61K 31/216* (2006.01)
*A61K 31/343* (2006.01)
*A61K 9/28* (2006.01)

(52) U.S. Cl.
CPC .......... *A61K 31/704* (2013.01); *A61K 9/2009* (2013.01); *A61K 9/2013* (2013.01); *A61K 9/2018* (2013.01); *A61K 9/2031* (2013.01); *A61K 9/2059* (2013.01); *A61K 9/2893* (2013.01); *A61K 31/045* (2013.01); *A61K 31/192* (2013.01); *A61K 31/216* (2013.01); *A61K 31/343* (2013.01); *A61K 36/258* (2013.01); *A61K 36/537* (2013.01)

(58) Field of Classification Search
CPC ...................................................... A61K 36/00
See application file for complete search history.

(56) References Cited

U.S. PATENT DOCUMENTS

2005/0037094 A1    2/2005  Yan et al.
2007/0071834 A1*   3/2007  Cheng ................. A61K 31/045
                                                424/725

FOREIGN PATENT DOCUMENTS

| CN | 1596920 A | 3/2005 |
|---|---|---|
| CN | 1600318 A | 3/2005 |
| CN | 1669573 A | 9/2005 |
| CN | 1714819 A | 1/2006 |
| CN | 1879697 A | 12/2006 |
| CN | 101085000 A | * 12/2007 |
| CN | 101085000 A | * 12/2007 |
| CN | 101279220 A | 10/2008 |
| CN | 101518495 A | 9/2009 |
| CN | 101612195 A | 12/2009 |
| EP | 2415749 A1 | 2/2012 |
| TW | 201117839 A | 6/2011 |
| WO | WO 2005/087242 A1 | 9/2005 |
| WO | WO 2012/016549 A1 | 2/2012 |

OTHER PUBLICATIONS

Yinggai Chen, Lesson of severe hypotension caused by intravenous infusion of nitroglycerin, Apr. 7, 1997, 2 pages, China Journal of Modern Medicine, Central Hospital, Shaoyang City, Hunan Province.
Mei Liu et al., Clinical Observation of Tolerance of intravenous infusion of nitroglycerin in elderly patients with CHD, May 1996, 5 pages, vol. 3, Southern Journal of Nursing.
New Pharmaceutics, Medicines for preventing angina pectoris, Apr. 1998, 2 pages, 14th version.
Jiping He, 5 cases of hypotension caused by nitroglycerin, May 25, 1996, 1 page, Shanxi Medical Journal.

* cited by examiner

*Primary Examiner* — Qiuwen Mi
(74) *Attorney, Agent, or Firm* — Reinhart Boerner Van Deuren P.C.

(57) ABSTRACT

A traditional Chinese medicine composition for treating cardiovascular disease, and a preparation thereof, particularly a micro drop pill preparation thereof, and a method for preparing the preparation; the method for preparing the micro drop pill preparation can be used to prepare drop pills, coated drop pills, and drop pill capsules with a high drug loading capacity.

10 Claims, 20 Drawing Sheets

TRADITIONAL CHINESE MEDICINE COMPOSITION, AND PREPARATION AND APPLICATION THEREOF

FIELD OF THE INVENTION

The present invention relates to a traditional Chinese medicine composition and a preparation thereof, more particular to a traditional Chinese medicine composition for treating cardiovascular disease and a preparation thereof, especially a micro drop pill preparation. Also, the present invention relates to a method for preparing the traditional Chinese medicine and the preparation thereof. Wherein, the method for preparing the micro drop pill preparation can be used to prepare the drop pills, coated drop pills and drop pill capsules with high drug-loading capacity.

BACKGROUND OF THE INVENTION

With the improvement of living standards, worldwide population aging and younger onset population, the patients with cerebral and cardiovascular diseases are increased year by year. It has become the second large disease that does harm to human health. Angina pectoris is a clinical syndrome which is characterized in chest pain and chest discomfort, caused by myocardial temporary ischemia and hypoxia. Coronary heart disease (CHD) angina pectoris means the pectoris induced by myocardial ischemia and hypoxia that is caused by coronary arteriosclerosis or spasm, accounting for about 90% of the patients with angina pectoris.

Now, the methods for treating angina pectoris are dominated by dilating vessels, reducing blood viscosity and inhibiting platelets aggregation as well as anticoagulation. Traditionally, the chemicals include the nitrate, nitrite, β-receptor blocker and calcium antagonist. However, due to the stronger toxicity and side effect, these drugs are not suitable to use for long time. In addition, most of them focus on symptomatic treatment with no more effect on disease progress. Occasionally, symptoms occur after administrating the nitroglycerin, for example the head pain, head throbbing, speed-up heartbeat and even syncope (see *New Pharmaceutics*, 14$^{th}$ edition, p 264). Recently, the nitroglycerin was reported to have problems of inducing severe hypotension (see *China Journal of Modern Medicine*, 1997, 7 (4): 42, *Shanxi Medicine Journal*, 1996, 25(2) 315) and of being prone to producing tolerance (see Nanfang Journal of Nursing, 1996, 3(5):7~9). Hence, this hindered its application in clinic.

Although a lot of traditional Chinese medicines have been used for treating angina pectoris, the pill, powder, ointment, Dan and decoction had become ancient history, which is seldom used by modern people. Now, there are common compound *Salvia* tablet and capsule commercially available. Because the production processes for the tablet and capsule are outdated, the content of active ingredients is low with no quality control indices. Both are absorbed into blood via the gastrointestinal tract after oral administration. Due to the hepatic first pass effect, they have low bioavailability and slow absorption, and are not competent to the first aid for the patients with angina pectoris.

Drop pill is a traditional preparation for traditional Chinese medicine. It has the following merits: reduced volatility of drug, increased drug stability, high bioavailability, quickened onset of effect, prolonged action in topical administration, shortened production cycle, dust pollution-free, and easily carried on.

However, the preparation method of traditional drop pill is to melt a medicine liquid and drop it into immiscible cooling medium to give the drop pill. Because the drop pill is formed by the factors of downwards gravity, surface tension of medicine liquid and internal stress, the unit drug loading capacity is small (usually, the drug loading capacity of API is about 25%) and the amount of matrix very large. This does not meet the requirement of international market that the maximum daily dose of PEG matrix should not exceed 700 mg. Moreover, it is difficult to prepare the traditional drop pill with diameter of less than 2.5 mm, so the patients have to take a lot of hard-to-swallow pills each time, which will not satisfy the fast-paced trend of modern life, and be prone to the problems of inaccurate dose. Thus, it is generally unacceptable by the international consumers. In addition, there are a number of shortcomings in the preparation of traditional drop pill, e.g. the low dropping rate, poor roundness and large variation on the pill weight and particle size, as well as small unit drug loading capacity and large amount of matrix (due to sufficient medium to ensure dropping effect). Because the cooling liquid has been used for solidifying the drop pill, the necessary step is needed in the sequent process to remove the cooling liquid, and the remaining cooling liquid may pose the problem of residual organic solvent. Besides, drying methods for the traditional drop pill have the defects of prolonged time, slow speed, uneven drying and easily leading to evaporation of volatile oil and precipitation of Borneol that is included in the products.

As a result of this, how to find a production process for preparing micro drop pills, regular drop pills and drop pill capsules that achieves high production rate, reduces amount of matrix and increases drug-loading capacity is an important subject in need of development and exploration of the modern formulation technique for drop pill.

Compound *Salvia* Drop Pill (CSDP) is a traditional Chinese medicine developed by Tasly Pharmaceutical Co., Ltd, which is proven to have the effects of activating blood by removing stasis as well as stopping pain by regulating Qi, used for treating chest distress and angina pectoris. The main ingredients of CSDP include *Salvia Miltiorrhiza, Panax Notoginseng* and Borneol. Its pharmacological effects include increasing coronary blood flow, protecting ischemia myocardium by strengthening hypoxia tolerance, anti-platelet aggregation, preventing thrombosis and improving microcirculation etc. Although the preparation of CSDP is known as a very mature technique in the prior art, there are still a lot of problems faced during preparation process, e.g. large amount of matrix and small drug-loading capacity.

CONTENT OF THE INVENTION

The objective of present invention is to provide a traditional Chinese medicine composition for treating acute myocardial infarction and acute myocardial ischemia. Said composition is composed of following materials by weight percentage: 50.0%~99.9% of *Salvia Miltiorrhiza* and *Panax Notoginseng* extract and 0.1%~50.0% of borneol. Wherein, the *Salvia Miltiorrhiza* and *Panax Notoginseng* extract comprises following ingredients by weight parts:

Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(2~6):(0.5~2):(1~3):(0.2~1):(0.2~1):(0.5~2):

(0.5~2):(0.2~1):(1~4):(0.1~0.5):(1~4):(0.1~1):(0.01~0.05): (0.05~0.1):(0.02~0.1):(0.1~0.5).

In an embodiment of this invention, said composition may be prepared into various kinds of preparations, such as injections, tablets, capsules, drop pills and micro drop pills, preferably the micro drop pill. Said micro drop pill means a smaller-sized drop pill than the traditional drop pill. In particular, said micro drop pill has the particle size of 0.2 mm~4 mm, especially 0.2 mm~2 mm, most preferably 1 mm~2 mm.

Another objective of present invention is to provide a compound *Salvia* micro drop pill (CSMDP). In said micro drop pill, the weight ratio of medicine to matrix is 1:5~5:1, and particle size 0.2 mm~4 mm. The preparation method for preparing said micro drop pill comprises the steps as follows:

Material melting step: heating and melting medicine and a drop pill matrix to obtain a molten medicine liquid;

Dropping step: delivering the molten medicine liquid to a dripper, and acquiring medicine drops of the molten medicine liquid by means of vibration dropping; and Condensation step: cooling the medicine drops with cooling gas to obtain micro drop pills.

In particular, the present invention comprises technical solutions as follows:

1. A traditional Chinese medicine composition composed of the following materials by weight percentage: 50.0%~99.9% of *Salvia Miltiorrhiza* and *Panax Notoginseng* extract and 0.1%~50.0% of borneol, wherein the *Salvia Miltiorrhiza* and *Panax Notoginseng* extract comprises following ingredients by weight percentage:

Danshensu:Salvianolic acid T:protocatechuic aldehyde: Salvianolic acid D:rosmarinic acid:Salvianolic acid B:Salvianolic acid A:*Panax Notoginseng Saponin R*1:Ginsenoside Rg1:Ginsenoside Re:Ginsenoside Rb1:Ginsenoside Rd:dihydrotanshinone I:tanshinone I:cryptotanshinone:tanshinone IIA=(2~6):(0.5~2):(1~3):(0.2~1):(0.2~1):(0.5~2): (0.5~2):(0.2~1):(1~4):(0.1~0.5):(1~4):(0.1~1):(0.01~0.05): (0.05~0.1):(0.02~0.1):(0.1~0.5).

2. The traditional Chinese medicine composition according to $1^{st}$ paragraph, wherein said composition is composed of following materials by weight percentage: 75.0%~99.9% of *Salvia Miltiorrhiza* and *Panax Notoginseng* extract and 0.1%~25.0% of borneol.

3. The traditional Chinese medicine composition according to $1^{st}$ paragraph, wherein said composition is composed of the following materials by weight percentage: 90.0%~99.9% of *Salvia Miltiorrhiza* and *Panax Notoginseng* extract and 0.1%~10.0% of borneol.

4. The traditional Chinese medicine composition according to any one of $1^{st}$~$3^{rd}$ paragraphs, wherein the *Salvia Miltiorrhiza* and *Panax Notoginseng* extract comprises following ingredients by weight parts:

Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(3~4):(0.9~1.2):(1.4~2.0):(0.5~0.7):(0.5~0.9): (1~1.6):(0.7~1.2):(0.5~0.9):(1.8~2.8):(0.2~0.4):(1.7~2.2): (0.2~0.6):(0.03~0.04):(0.07~0.08):(0.05~0.06):(0.26~0.28).

5. The traditional Chinese medicine composition according to $4^{th}$ paragraph, wherein the *Salvia Miltiorrhiza* and *Panax Notoginseng* extract comprises following ingredients by weight parts:

Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=3.6:1.1:1.7:0.6:0.7:1.3:0.9:0.7:2.4:0.3:1.8:0.4: 0.03:0.07:0.06:0.27.

6. The traditional Chinese medicine composition according to any one of $1^{st}$~$3^{rd}$ paragraphs, wherein the *Salvia Miltiorrhiza* and *Panax Notoginseng* extract is prepared with following crude medicine by weight parts: *Salvia Miltiorrhiza* 75~90 parts and *Panax Notoginseng* 10~25 parts.

7. The traditional Chinese medicine composition according to $6^{th}$ paragraph, wherein the *Salvia Miltiorrhiza* and *Panax Notoginseng* extract is prepared with following crude medicine by weight parts: *Salvia Miltiorrhiza* 82~84 parts, *Panax Notoginseng* 16~17 parts.

8. A pharmaceutical preparation comprising the traditional Chinese medicine composition according to any one of s$1^{st}$~$7^{th}$ paragraphs and pharmaceutically acceptable carriers.

9. The pharmaceutical preparation according to $8^{th}$ paragraph, wherein said preparation is in a dosage form of drop pill or micro drop pill, preferably the micro drop pill, wherein said micro drop pill is prepared with the traditional Chinese medicine composition and the drop pill matrix in a ratio of 1:5~5:1 by weight.

10. A compound *Salvia* micro drop pill, wherein said micro drop pill is prepared with the traditional Chinese medicine composition according to any one of $1^{st}$~$7^{th}$ paragraphs and drop pill matrix in a ratio of 1:5~5:1 by weight.

11. The preparation method for the micro drop pill according to $10^{th}$ paragraph, comprising following steps:

(1) Material melting step: charging said medicine and matrix into a homogenizer, mixing homogenously at 1000~5000 rpm for 1~200 min, melting homogenously at 3000~10000 rpm for 1~100 min; during the melting process, the temperature is kept at 60~100° C. to obtain the molten medicine liquid; said ratio of medicine to the micro drop pill matrix is 1:5~5:1 by weight;

(2) Dropping step: delivering the molten medicine liquid to a dripper, and acquiring medicine drops from the dripper by means of vibration dropping at a vibration frequency of 2~2000 Hz under a dropping pressure of 0.5~4.0 Bar, with an acceleration at 1~20 G; the temperature of the dripper is at 70~300° C.; the dropping rate is matched with the melting rate in step (1); and (3) Condensation step: cooling the medicine drops with cooling gas rapidly to solidify and obtaining the solid drop pill having a particle size of 0.2 mm~4.0 mm; the temperature of the cooling gas is 0° C. or lower.

12. The preparation method according to $11^{th}$ paragraph, wherein in step (1), said drop pill matrix includes one or more of PEG, sorbitol, xylitol, lactitol, maltose, starch, methylcellulose, sodium carboxymethyl cellulose, hydroxypropyl methylcellulose (HPMC), Arabic gum, alginate, dextrin, cyclodextrin, agar and lactose, preferably the solid PEG, e.g. PEG-1000, PEG-2000, PEG-3000, PEG-4000, PEG-5000, PEG-6000, PEG-7000 and PEG-8000, more preferably one or more of the PEG-1000, PEG-2000, PEG-3000, PEG-4000, PEG-6000, PEG-8000, most preferably the PEG-6000, PEG-4000, or the combination of PEG-4000 and PEG-6000.

13. The preparation method according to $11^{th}$ or $12^{th}$ paragraph, wherein said method comprises the following steps:

(1) Material melting step: charging the medicine and matrix into a homogenizer, mixing homogenously at 1000~5000 rpm, melting homogenously at 3000~10000 rpm for 20~80 min; during the melting process, the temperature is kept at 80~100° C. to obtain the molten medicine liquid; the ratio of the medicine to the micro drop pill matrix is 1:3~3:1 by weight;

(2) Dropping step: delivering the molten medicine liquid to a dripper, and acquiring medicine drops from the dripper by means of vibration dropping at a vibration frequency of 20~300 Hz under a dropping pressure of 0.5~4.0 Bar, with an acceleration at 1~15 G; the temperature of the dripper is at 70~200° C.; the dropping rate is matched with the melting rate in step (1); and (3) Condensation step: cooling the medicine drops with cooling gas rapidly to solidify and obtaining solid drop pill having a particle size of 0.2 mm~4.0 mm; the temperature of the cooling gas is 0° C. or lower.

14. The preparation method according to $12^{th}$ paragraph, wherein in step (1), the ratio of the medicine to the drop pill matrix is 1:3~3:1 by weight, mixing homogeneously 3000~5000 rpm for 10~60 min and melting homogeneously at 4000~9000 rpm for 5~30 min, during the melting process, the temperature is kept at 70~90° C.; preferably, the ratio of the medicine to the matrix is 1:(1~3) by weight, mixing homogeneously 3000~4000 rpm for 10~30 min and melting homogeneously at 4000~6000 rpm for 6~30 min, and during the melting process the temperature is kept at 75~85° C.

15. The preparation method according to $12^{th}$ paragraph, wherein in step (2), the temperature of the dripper is at 70~100° C., preferably at 75~85° C.; the vibration frequency is at 50~300 Hz, preferably at 100~200 Hz, more preferably at 90~200 Hz, more preferably at 130~140 Hz, most preferably at 137 Hz; the acceleration is at 3.5~4.5 G, preferably at 4.0 G; the dropping pressure is at 1.0~3.0 Bar, preferably at 1.8 Bar; and the dropping rate is 10~40 kg/h, preferably 12~30 kg/h, further preferably 15~25 kg/h.

16. The preparation according to $12^{th}$ paragraph, wherein in step (3), the cooling gas is selected from air, nitrogen and inert gas; the temperature of the cooling gas is 0~−150° C., preferably −60~−140° C., more preferably −80~−120° C.; the particle size is 1.0 mm~2.0 mm.

17. The preparation method according to any one of $11^{th}$~$16^{th}$ paragraphs, wherein said method may additionally comprise step (4) of drying: fluidized-bed drying to perform drying at −20~100° C., preferably −20~90° C., for 1~4 hours to obtain a blank drop pill.

18. The preparation method according to $17^{th}$ paragraph, wherein a low-temperature drop pill from step (3) is dried with fluidized bed at 40~150° C., preferably 40~60° C. for 1~4 hours, preferably 1~3 hours, most preferably 2 hours, to obtain the blank pill.

19. The preparation method according to $18^{th}$ paragraph, wherein in step (4), gradient-rising temperature drying method is used as follows: fluidizing at −20~30° C., drying at 15~35° C. for 10~120 min, drying at 35~55° C. for 10~60 min, drying at 55~100° C. for 0~60 min; preferably fluidizing at 0~20° C., drying at 25° C. for 60 min, drying at 45° C. for 30 min, drying at 55° C. for 0~30 min.

20. The preparation method according to any one of $11^{th}$~$19^{th}$ paragraphs, wherein said method may additionally comprise step (5) of coating: coating the blank pill obtained from step (4) in a state of fluidization under 30~65° C.; wherein the concentration of coating liquid is at 5~25 wt %, preferably 18~20 wt %; coating material is selected from shellac, CAP (cellulose acetate phthalate), methyl acrylate, methyl methacrylate or opadry; the ratio of the coating material to the blank drop pill is 1:50~1:10, preferably 1:50~1:25.

21. The preparation method according to any one of $11^{th}$~$20^{th}$ paragraphs, wherein said method may additionally comprise a premixing step before step (1): adding medicine powder or extract with water, stirring for 10 min or longer at 30~80° C. to obtain a premixed medicine material.

22. Use of the traditional Chinese medicine composition according to $1^{st}$~$7^{th}$ paragraphs in preparation of a medicament for treating acute myocardial infarction and acute myocardial ischemia.

DETAILED EMBODIMENTS

Figure 1A:
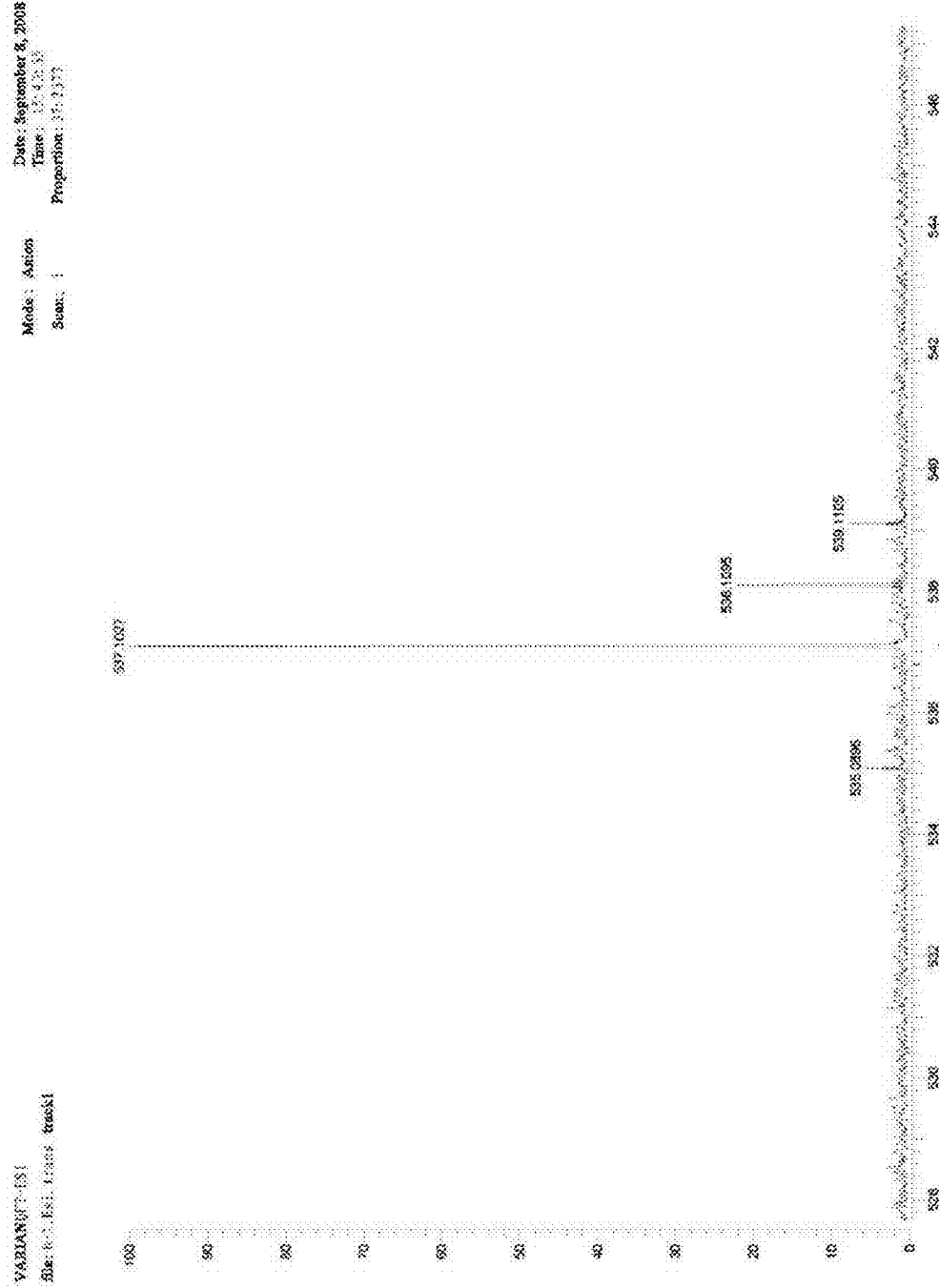
FIG. 1 was the high resolution mass spectrum of salvianolic acid T, A: (R)-salvianolic acid T; B: (S)-salvianolic acid T.
Figure 1B:
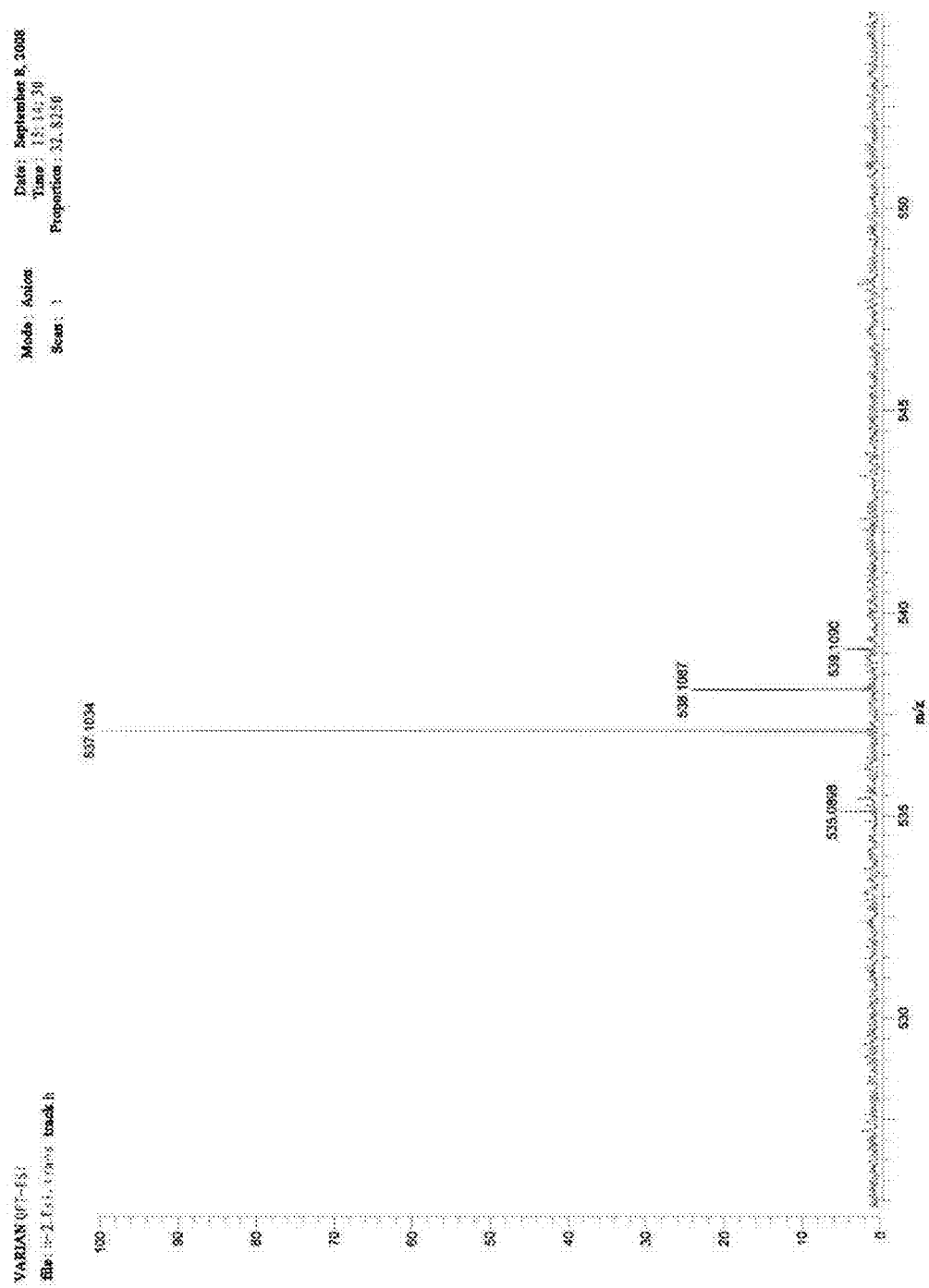
Figure 2A:
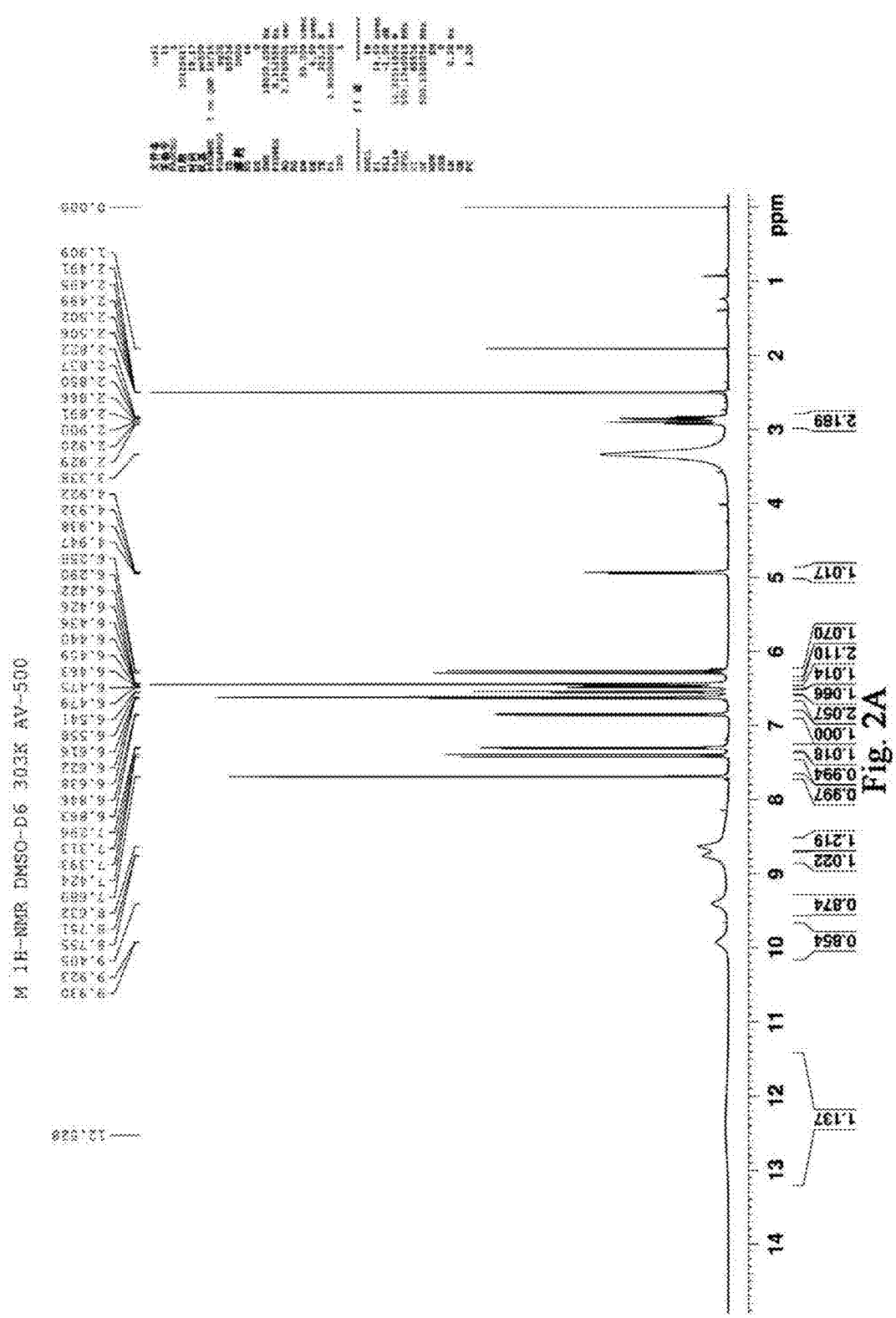
FIG. 2 was the $^1$H-NMR spectrum of salvianolic acid T (500 MHz, DMSO), A: (R)-salvianolic acid T; B: (S)-salvianolic acid T.
Figure 2B:
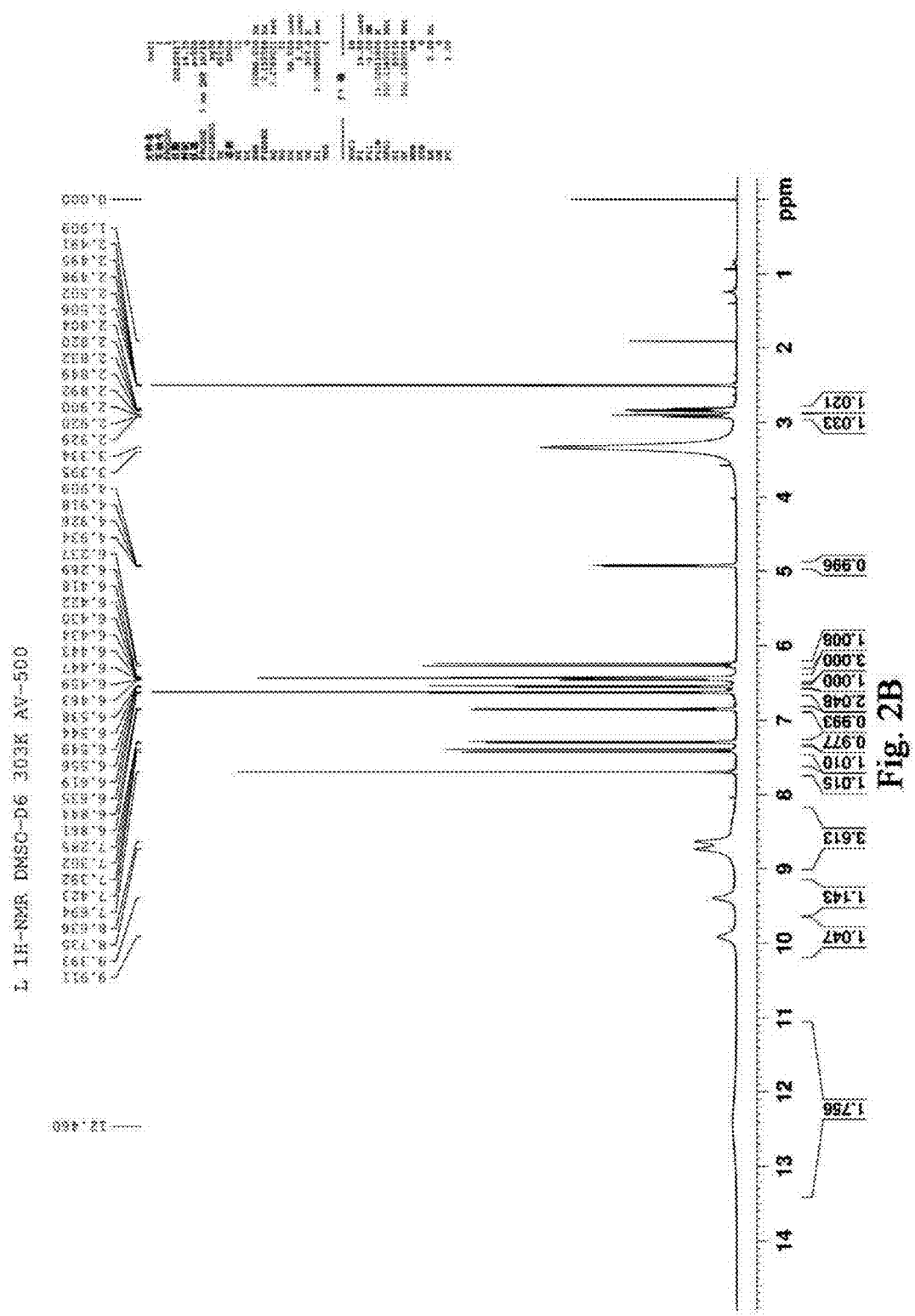
Figure 3A:
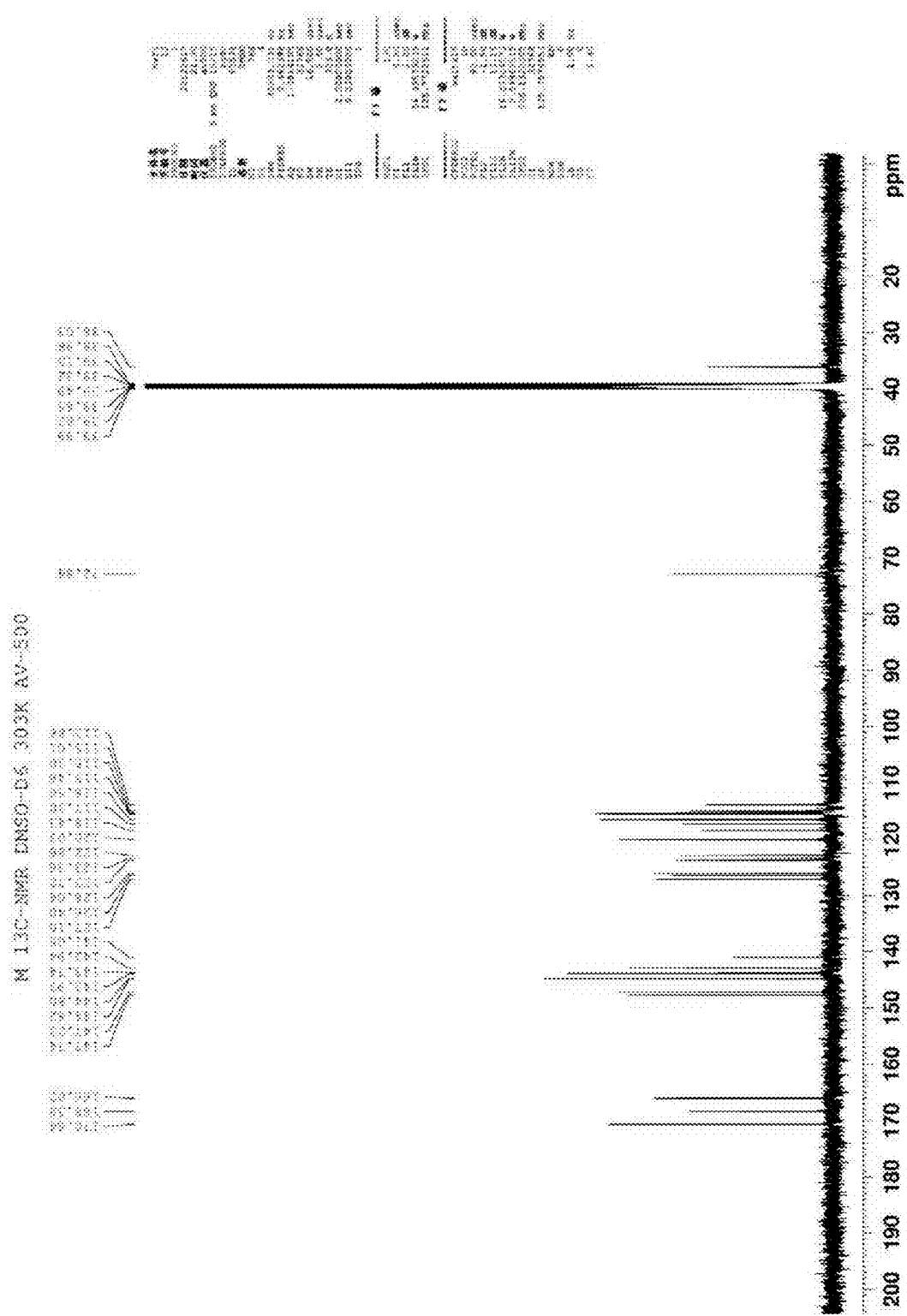
FIG. 3 was the $^{13}$C-NMR spectrum of salvianolic acid T (125 MHz, DMSO), A: (R)-salvianolic acid T; B: (S)-salvianolic acid T.
Figure 3B:
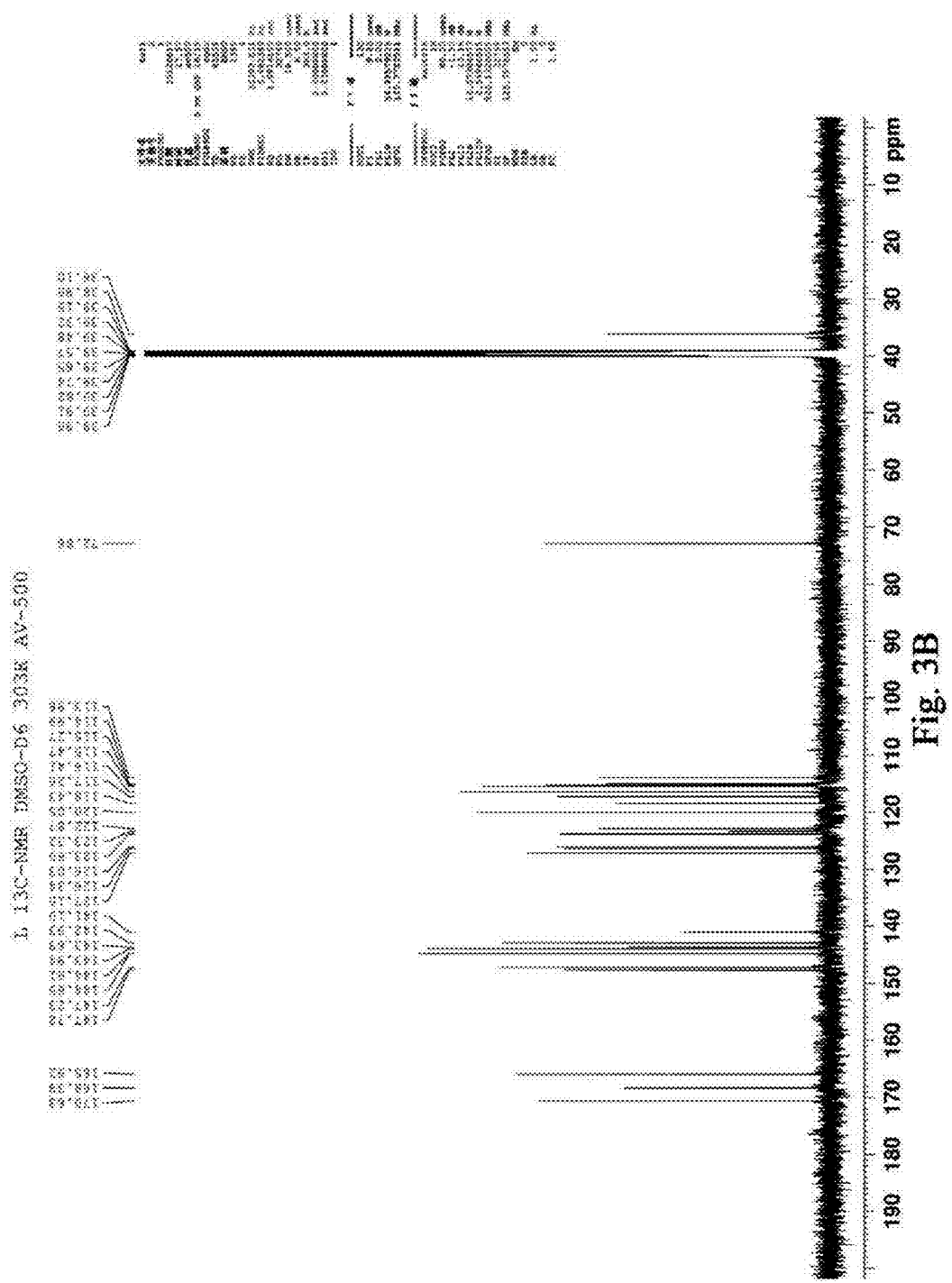
Figure 4A:
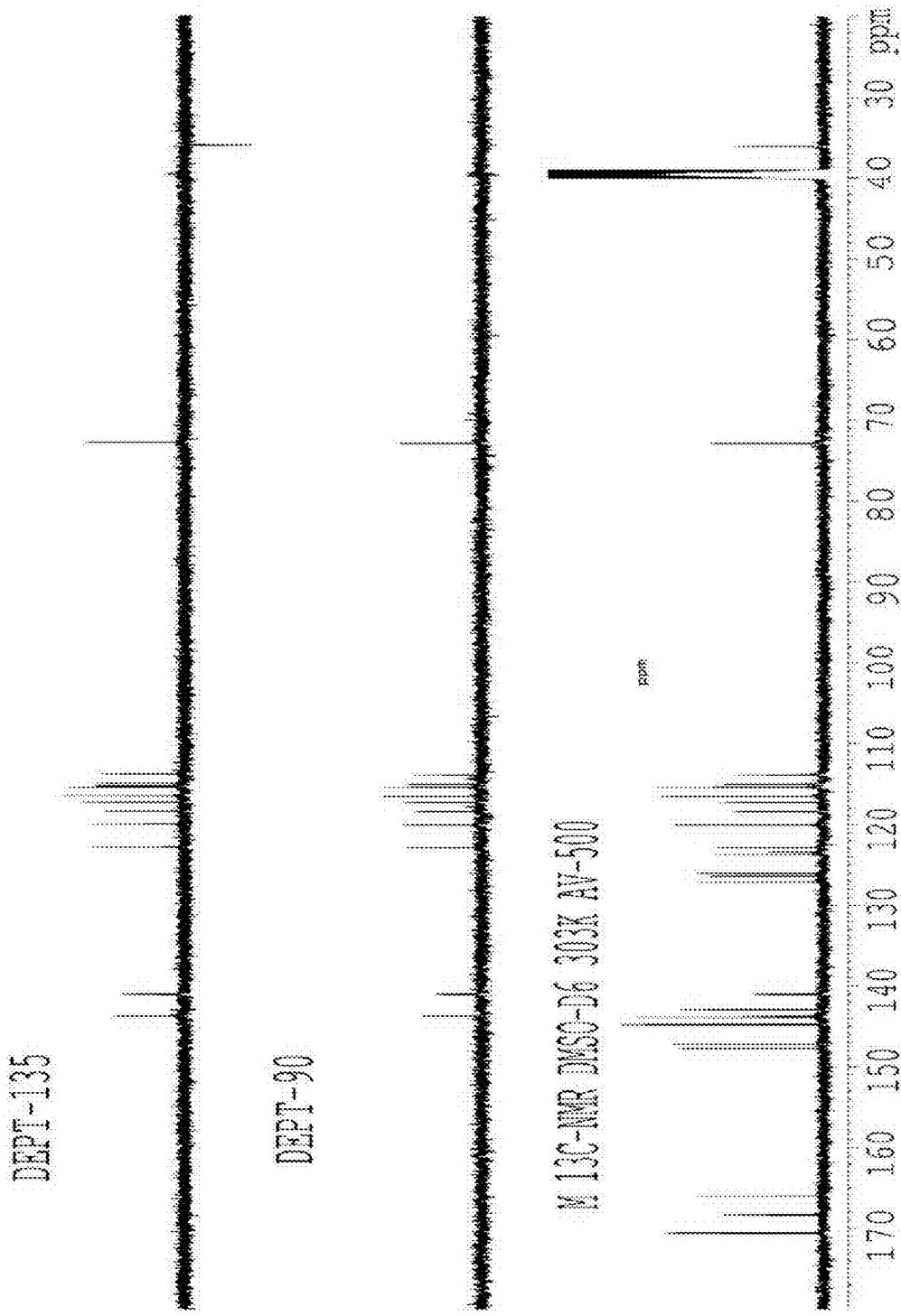
FIG. 4 was the DEPT spectrum of salvianolic acid T, A: (R)-salvianolic acid T; B: (S)-salvianolic acid T.
Figure 4B:
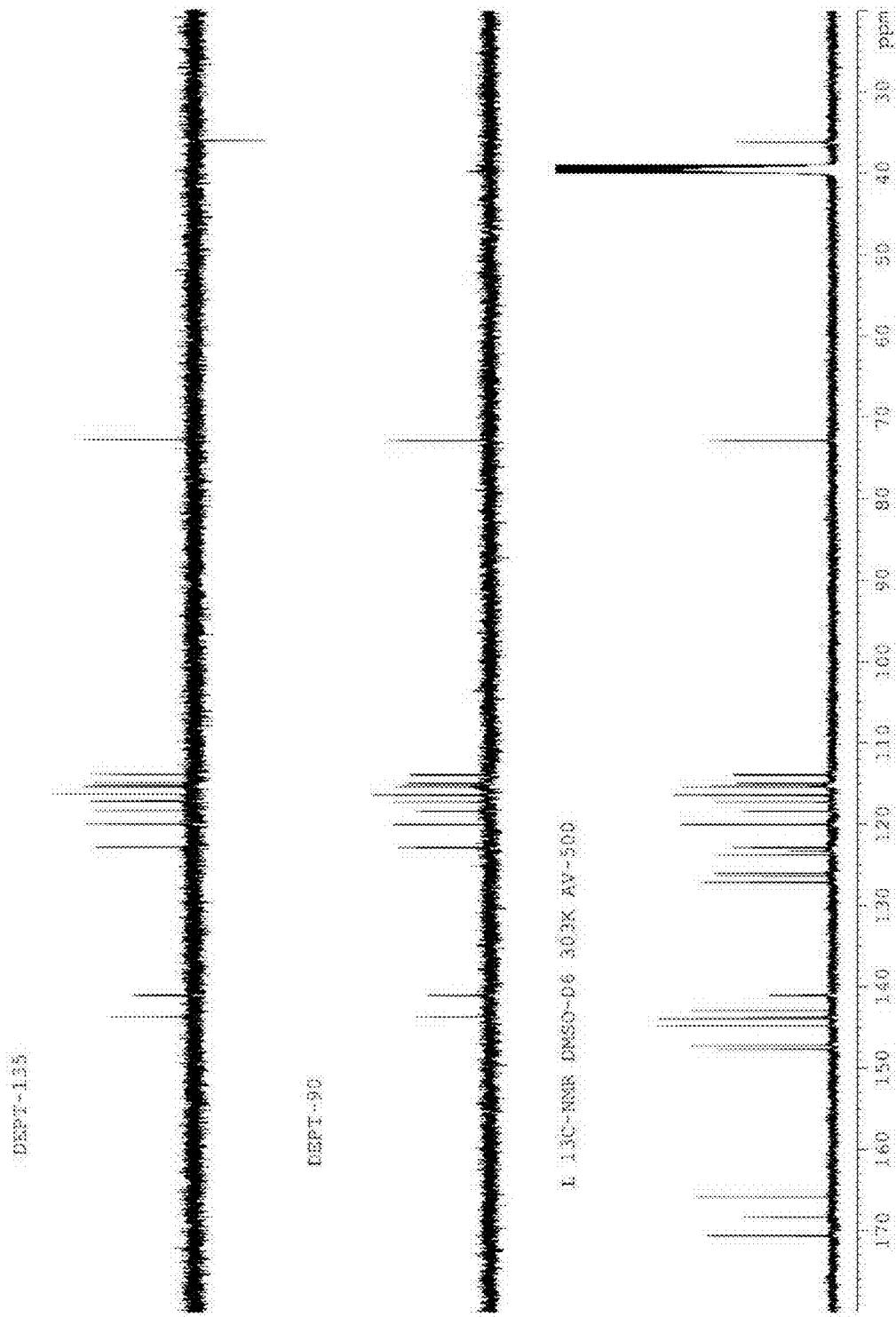
Figure 5A:
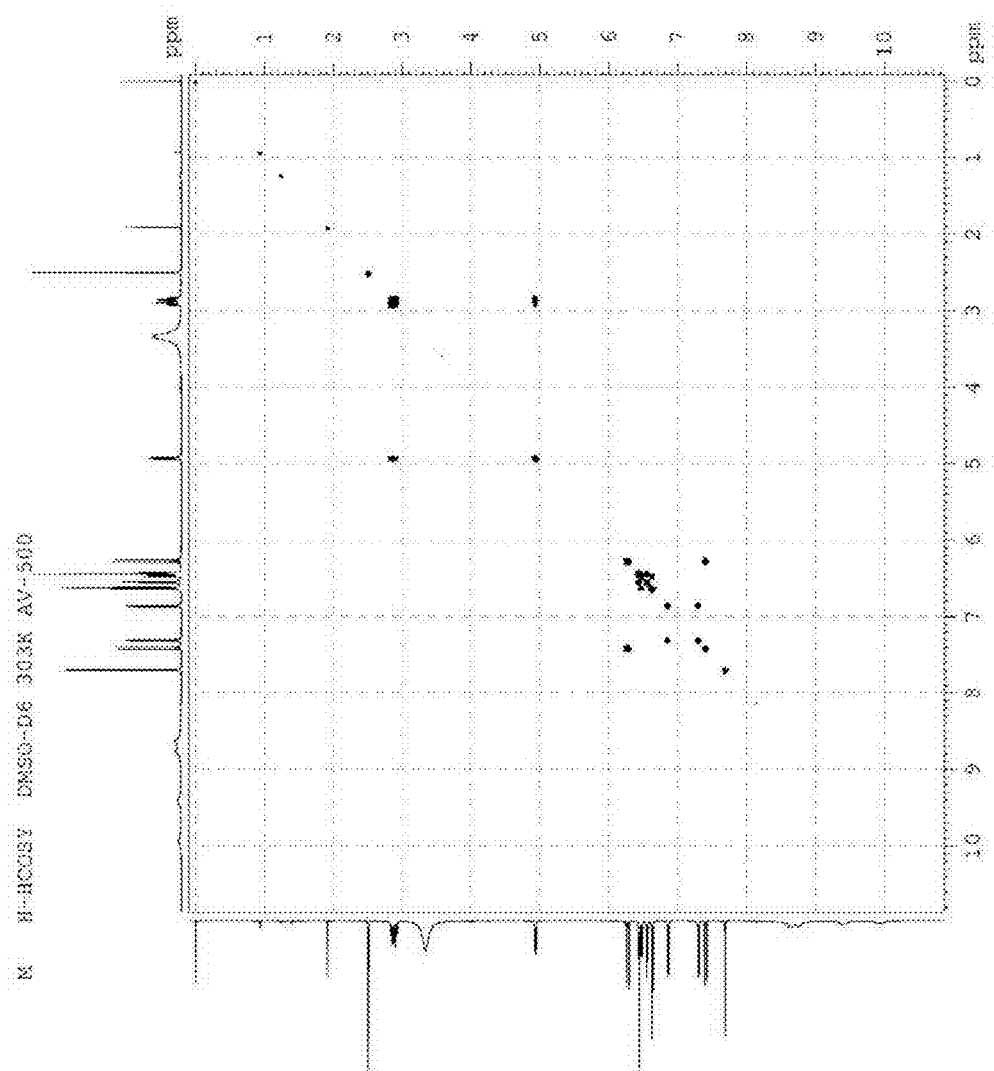
FIG. 5 was the COSY spectrum of salvianolic acid T, A: (R)-salvianolic acid T; B: (S)-salvianolic acid T.
Figure 5B:
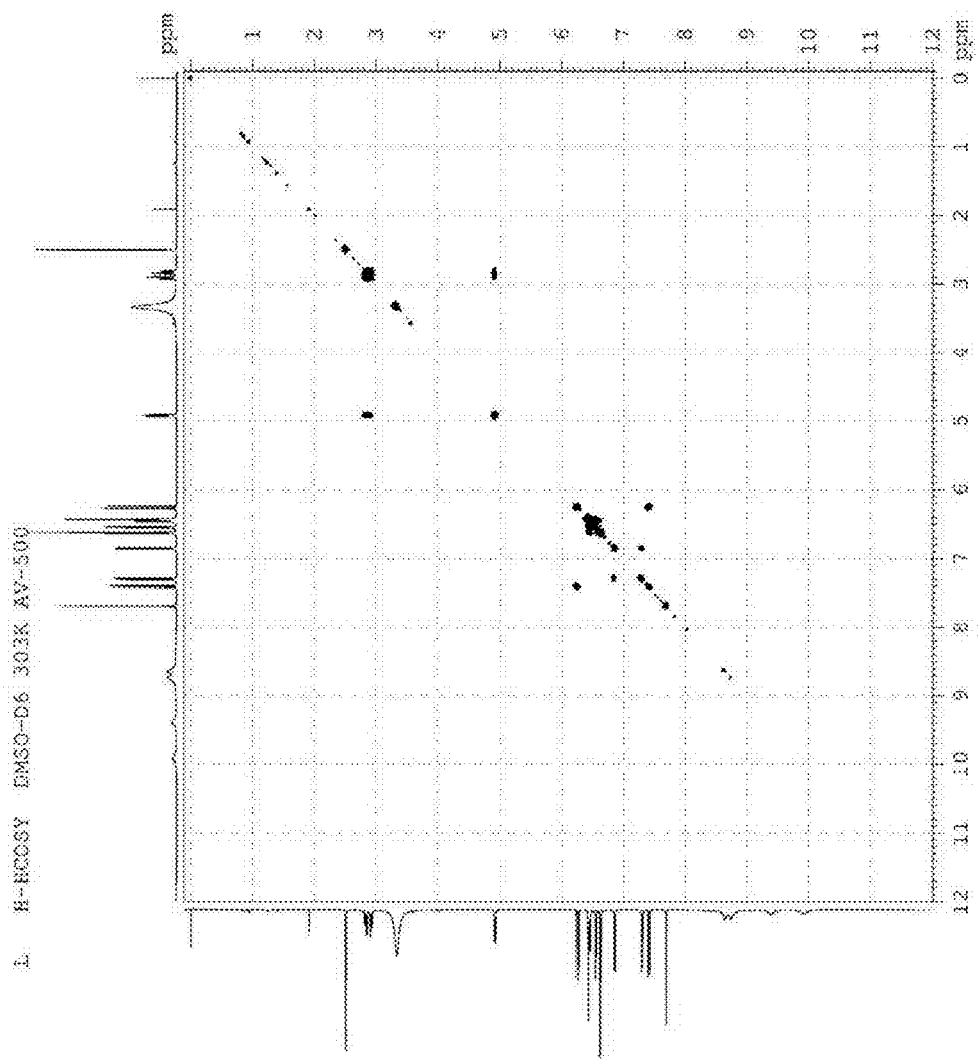
Figure 6A:
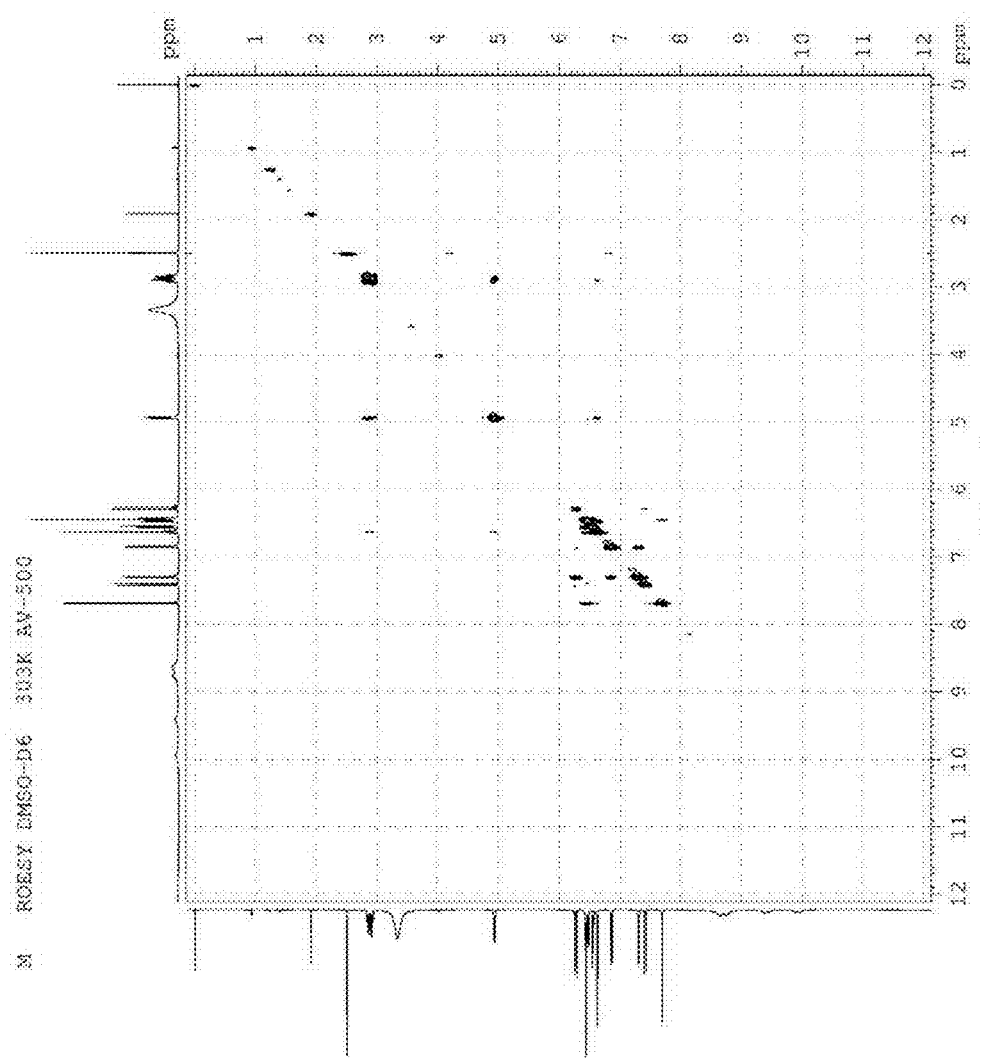
FIG. 6 was the ROESY spectrum of salvianolic acid T, A: (R)-salvianolic acid T; B: (S)-salvianolic acid T.
Figure 6B:
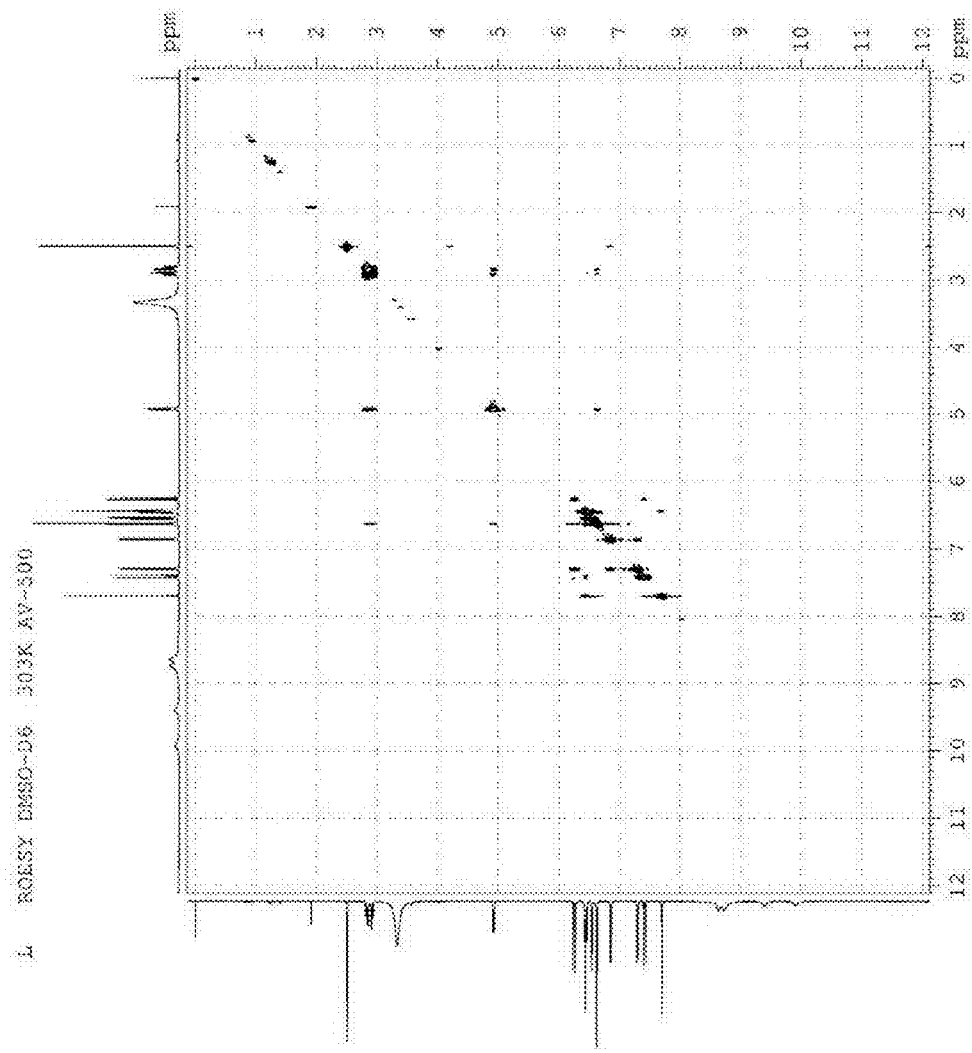
Figure 7A:
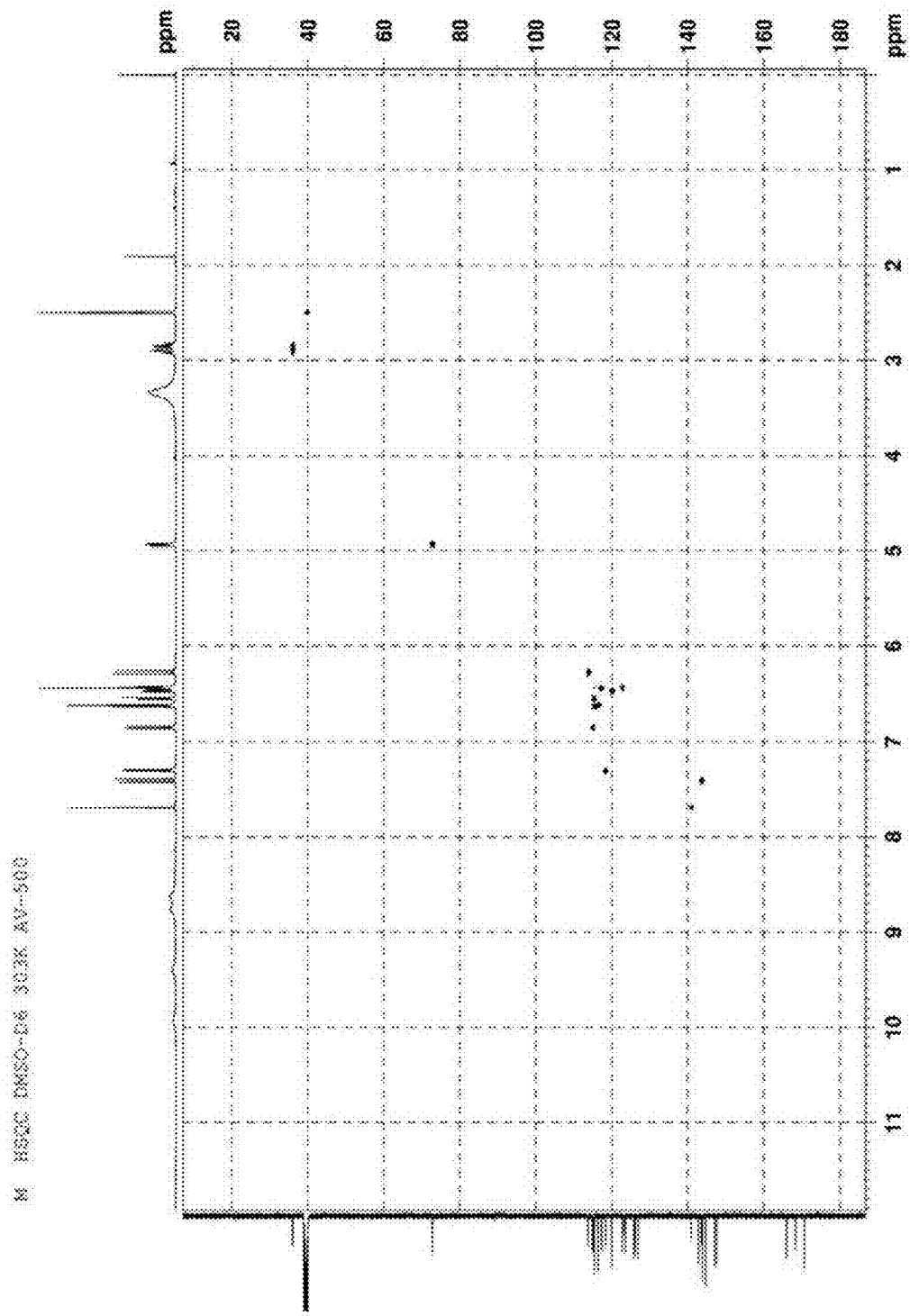
FIG. 7 was the HSQC spectrum of salvianolic acid T, A: (R)-salvianolic acid T; B: (S)-salvianolic acid T.
Figure 7B:
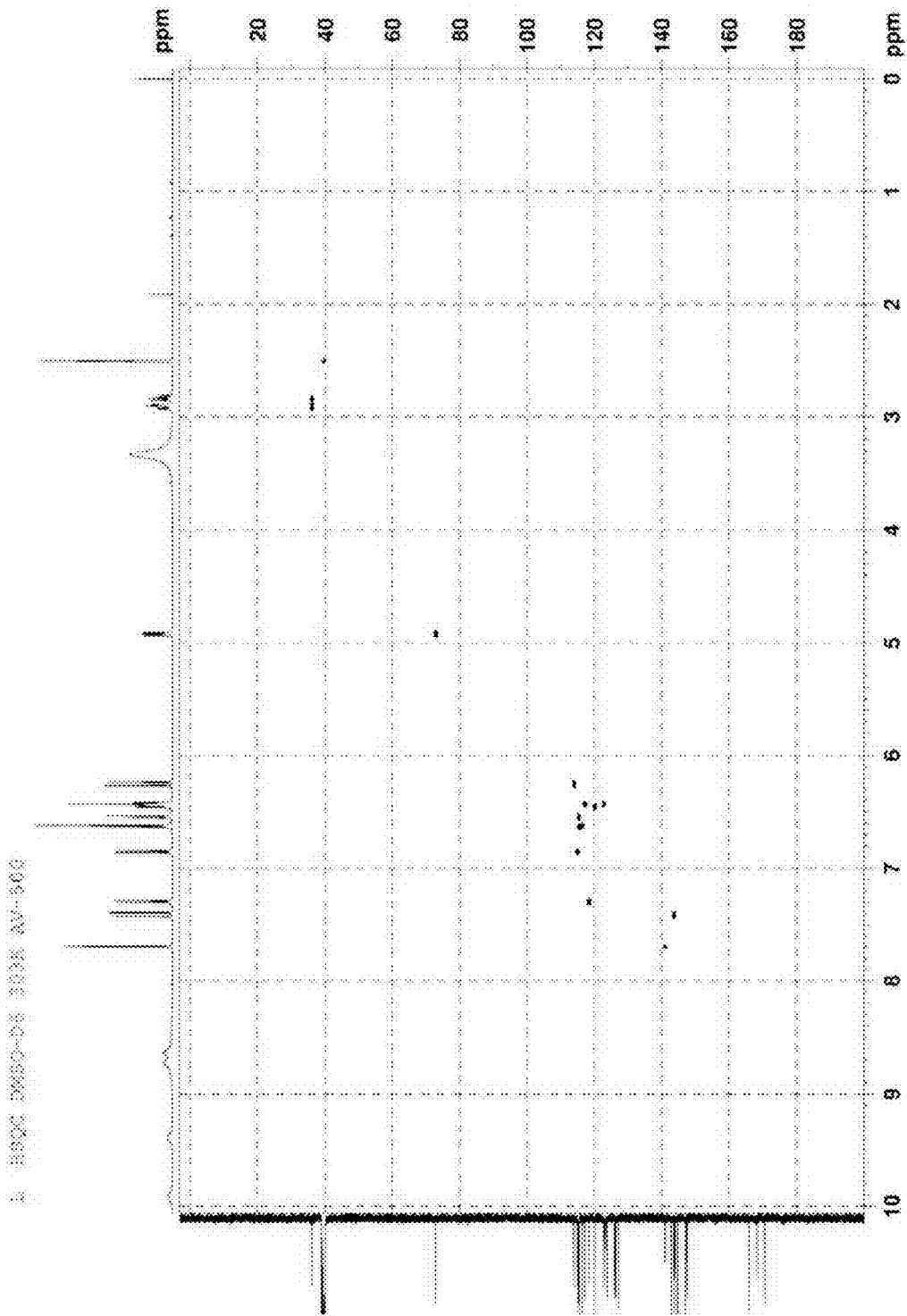
Figure 8A:
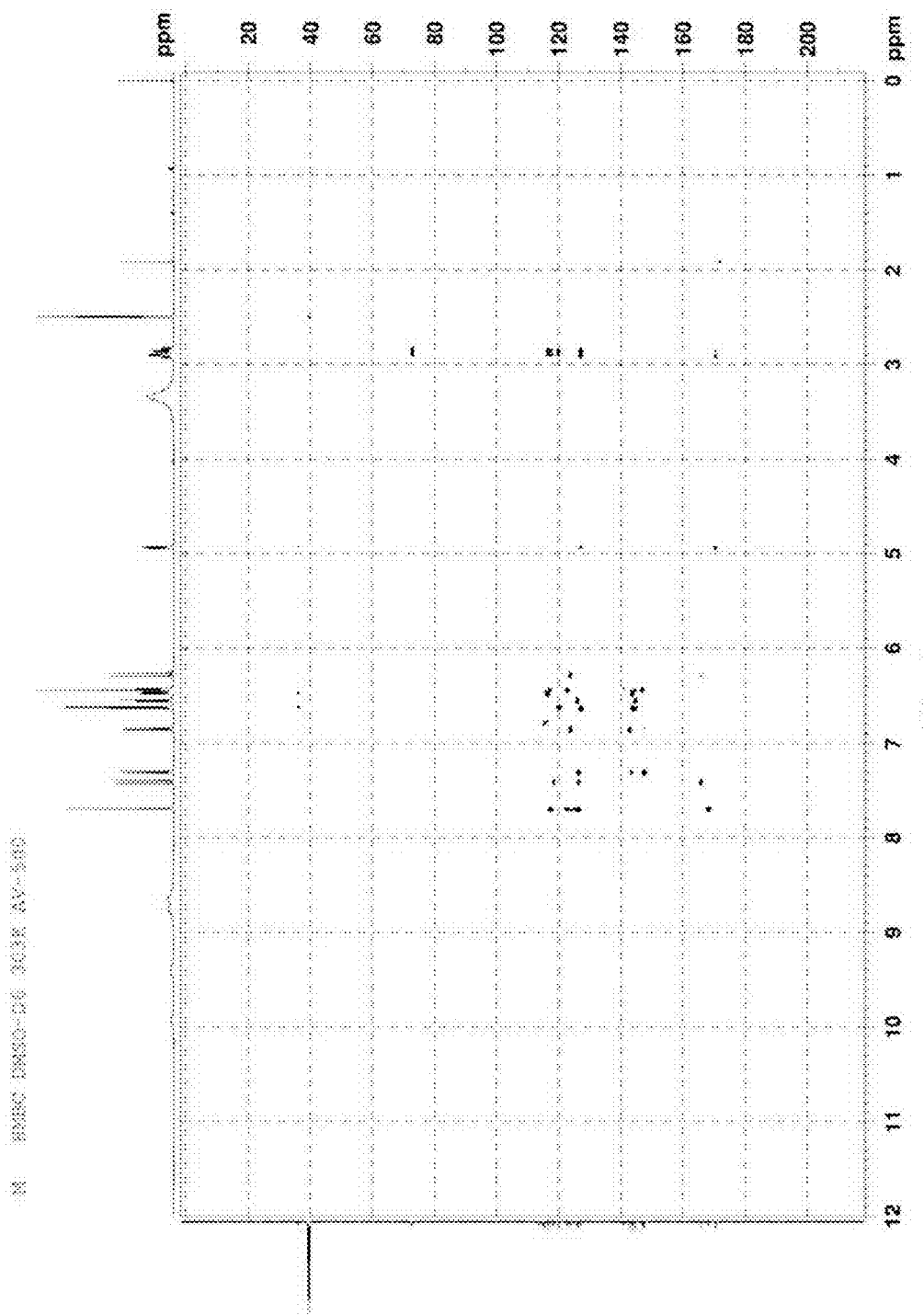
FIG. 8 was the HMBC spectrum of salvianolic acid T, A: (R)-salvianolic acid T; B: (S)-salvianolic acid T.
Figure 8B:
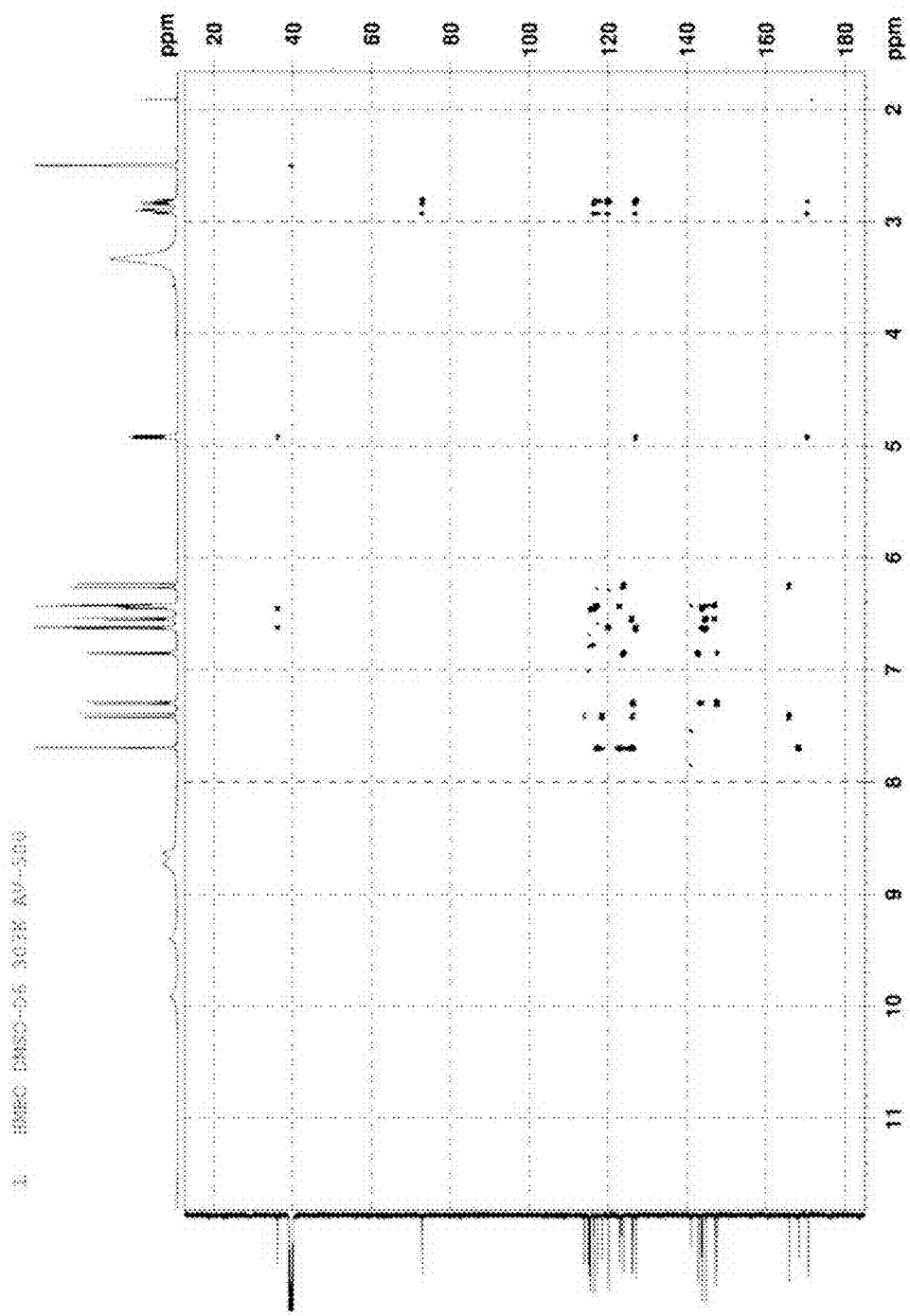
Figure 9A:
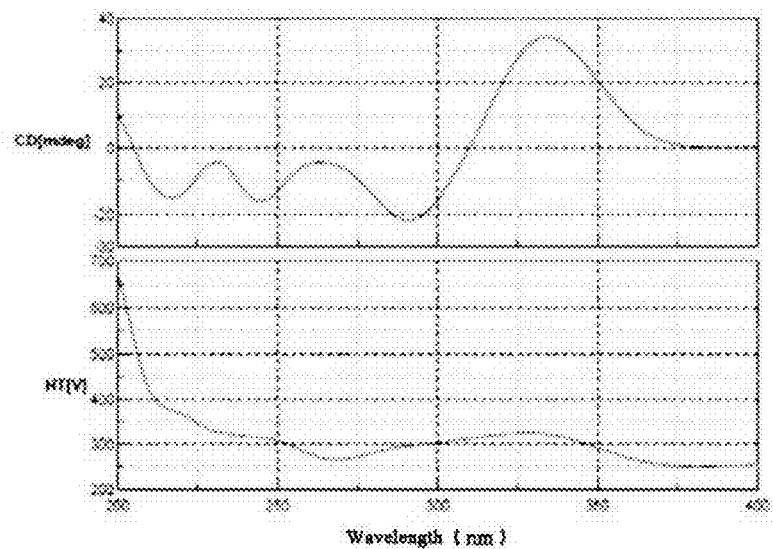
FIG. 9 was the CD spectrum of salvianolic acid T, A: (R)-salvianolic acid T; B: (S)-salvianolic acid T.
Figure 9B:
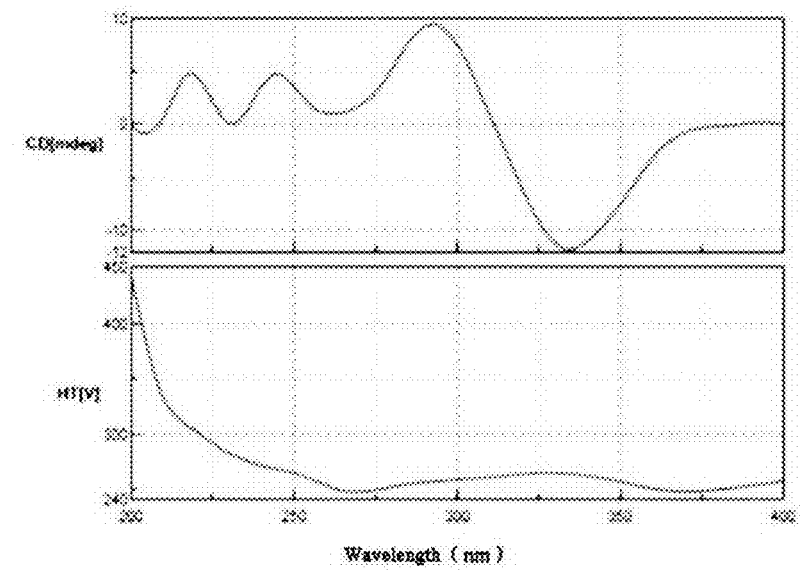
Figure 10A:
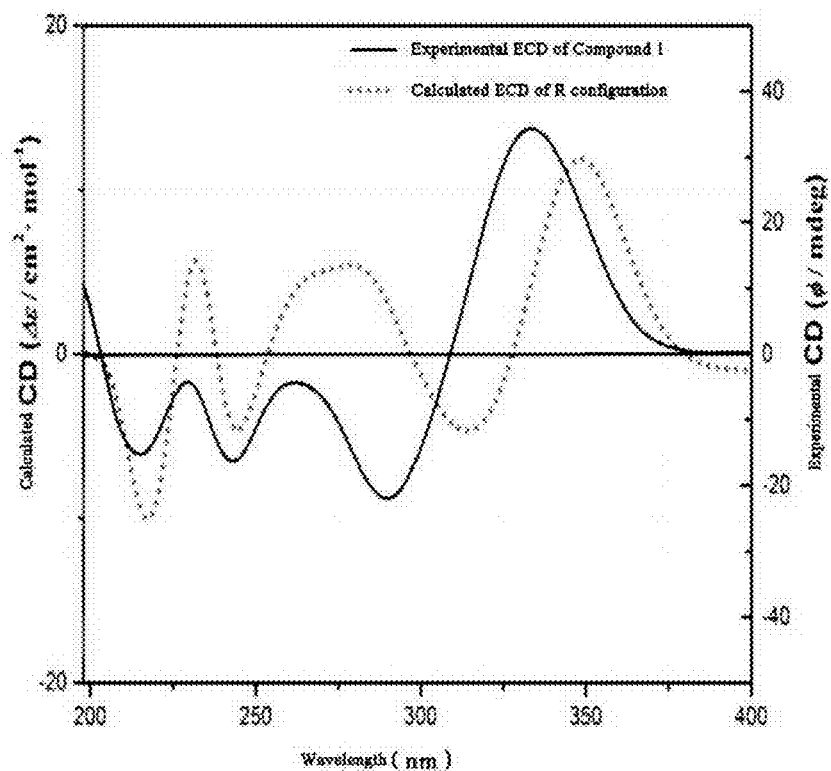
FIG. 10 was the comparison of CD spectrum and ECD simulated spectrum, A: (R)-salvianolic acid T; B: (S)-salvianolic acid T.
Figure 10B:
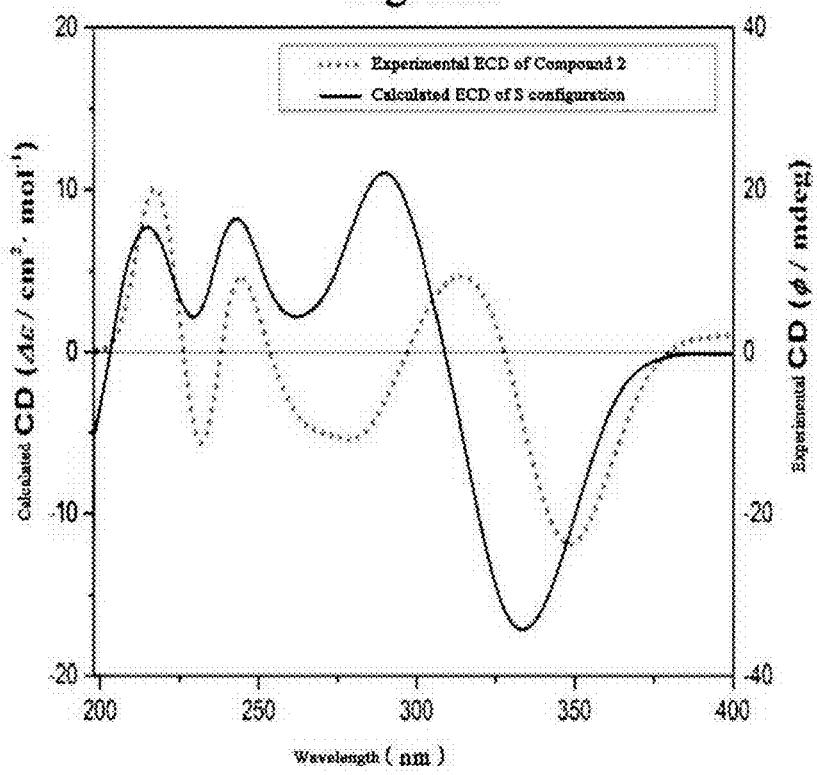

In an embodiment of this invention, the present invention is to provide a traditional Chinese medicine composition. Said composition is composed of following materials by weight percentage: 50.0%~99.9% of *Salvia Miltiorrhiza* and *Panax Notoginseng* extract and 0.1%~50.0% of borneol. Wherein, the *Salvia Miltiorrhiza* and *Panax Notoginseng* extract comprises following ingredients by weight percentage:

Danshensu:Salvianolic acid T:protocatechuic aldehyde:Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(2~6):(0.5~2):(1~3):(0.2~1):(0.2~1):(0.5~2):(0.5~2):(0.2~1):(1~4):(0.1~0.5):(1~4):(0.1~1):(0.01~0.05):(0.05~0.1):(0.02~0.1):(0.1~0.5).

Preferably, said composition is composed of following materials by weight percentage: 75.0%~99.9% of *Salvia Miltiorrhiza* and *Panax Notoginseng* extract and 0.1%~25.0% of borneol.

More preferably, said composition is composed of following materials by weight percentage: 90.0%~99.9% of *Salvia Miltiorrhiza* and *Panax Notoginseng* extract and 0.1%~10.0% of borneol.

Preferably, the *Salvia Miltiorrhiza* and *Panax Notoginseng* extract comprises following ingredients by weight parts:

Danshensu:Salvianolic acid T:protocatechuic aldehyde:Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(3~4):(0.9~1.2):(1.4~2.0):(0.5~0.7):(0.5~0.9):(1~1.6):(0.7~1.2):(0.5~0.9):(1.8~2.8):(0.2~0.4):(1.7~2.2):(0.2~0.6):(0.03~0.04):(0.07~0.08):(0.05~0.06):(0.26~0.28).

More preferably, the *Salvia Miltiorrhiza* and *Panax Notoginseng* extract comprises following ingredients by weight parts:

Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=3.6:1.1:1.7:0.6:0.7:1.3:0.9:0.7:2.4:0.3:1.8:0.4: 0.03:0.07:0.06:0.27.

In an embodiment of this invention, aforesaid traditional Chinese medicine composition is prepared by extracting *Salvia Miltiorrhiza* and *Panax Notoginseng* to give the extract, adding the borneol into the extract and mixing to have the product.

Preferably, the traditional Chinese medicine is prepared by the following method:

(1) Decocting *Salvia Miltiorrhiza* and *Panax Notoginseng* with water under alkaline conditions to give the decoction, filtering the decoction, concentrating and precipitating the filtrate with alcohol to get the supernatant, filtering the supernatant, recovering the alcohol to give the extract (or further drying the extract), namely the *Salvia Miltiorrhiza* and *Panax Notoginseng* extract;

(2) Adding the extract of above step with borneol and mixing uniformly.

Wherein, *Salvia Miltiorrhiza* and *Panax Notoginseng* may be decocted with water under alkaline condition either alone, or in combination.

Preferably, the *Salvia Miltiorrhiza* and *Panax Notoginseng* extract is prepared by following method:

(1) *Salvia Miltiorrhiza* and *Panax Notoginseng* are decocted with alkaline water solution for 1~3 times, 1~3 hours each time and filtered to get the filtrate I for later use;

(2) Resultant residue is decocted with water for 1~3 times, 1~3 hours each time, filtered to get the filtrate II for later use;

(3) The filtrate I and filtrate II are combined and concentrated to have the concentrated liquid, which is precipitated with alcohol and allowed to stand still to get the supernatant; the supernatant is taken, filtered, the alcohol was recovered and concentrated to give the extract (or drying the extract), namely the *Salvia Miltiorrhiza* and *Panax Notoginseng* extract.

Wherein, said alkaline water solution includes, but not limited to, one or more of sodium bicarbonate, sodium carbonate, sodium hydrogen phosphate, sodium dihydrogen phosphate, sodium hydroxide, potassium hydroxide and magnesium hydroxide with the pH value of 7.5~9.0; the concentration of the alkaline water solution is 1~4.5 wt %, preferably 2.25~3 wt %, ensuring that Danshensu and salvianolic acid T can be extracted totally.

In step (3), 50~100% (v/v) ethanol, most preferably 95% ethanol, was added to perform ethanol-precipitation, the final content of ethanol preferably 60~75% (v/v).

More preferably, the *Salvia Miltiorrhiza* and *Panax Notoginseng* extract is prepared by the following method:

(1) *Salvia Miltiorrhiza* is cut to 5 cm or smaller in length, preferably 1~2 cm, and *Panax Notoginseng* is ground into particles of 1 cm; sodium bicarbonate accounting for 2.25~3 wt % of total crude medicine is weighed and charged into an extracting tank together with weighed *Salvia Miltiorrhiza* and *Panax Notoginseng*; in each tank, 5 times of water is added to heat and keep boiling for 2 h±20 min and filtered;

(2) Resultant residue is extracted for $2^{nd}$ time by adding 4 times of water to heat and keep boiling for 1 h±15 min, filtered and the residue was removed;

(3) Afore-obtained extraction liquid is concentrated under reduced pressure to a relative density of 1.16~1.20 (80±5° C.) or corresponding sugar degree of 48~52% to give the concentrated liquid; the concentrated liquid is delivered to a alcohol precipitating tank, into which an appropriate amount of alcohol is added to make the final content of alcohol at 65~70% and allowed to stand still for 12~24 hours until complete precipitation; the supernatant is taken with the deposit removed; the supernatant is concentrated or dried to give the extract, namely the *Salvia Miltiorrhiza* and *Panax Notoginseng* extract.

Wherein, in step (1), 5 times of water means that the water is 5 times of total crude medicine in weight. Similarly, in step (2), 4 times of water means that the water is 4 times of total residue in weight.

In an embodiment of this invention, said traditional Chinese medicine composition is prepared by following crude medicine by weight parts: *Salvia Miltiorrhiza* 75~90 parts, *Panax Notoginseng* 10~25 parts and Borneol 0.1~4 parts.

Preferably, said traditional Chinese medicine composition is prepared by following crude medicine by weight parts: *Salvia Miltiorrhiza* 80~86 parts, *Panax Notoginseng* 15~18 parts and Borneol 0.2~2 parts.

Most preferably, said traditional Chinese medicine composition is prepared by following crude medicine by weight parts: *Salvia Miltiorrhiza* 82~84 parts, *Panax Notoginseng* 16~17 parts and Borneol 0.4~1.2 parts.

In an embodiment of this invention, said traditional Chinese medicine composition is either extract or powder.

In an embodiment of this invention, during the process for detecting the bioactive ingredients of *Salvia Miltiorrhiza* and *Panax Notoginseng* extract, it is first time to discover bioactive ingredients in aforesaid ratio by weight, and first time to separate and obtain new compound of salvianolic acid T.

In an embodiment of this invention, the structure of new compound of salvianolic acid was identified in its physicochemical properties, high resolution mass spectrum (QFT-ESI), electrospray ionization mass spectrum (ESI-MS), $^1$H-NMR, $^{13}$C-NMR, DEPT, COSY, HMBC, HMQC and CD spectra (FIGS. 1~10).

The structure of the new compound of salvianolic acid is represented by the general formula (I) as follows,

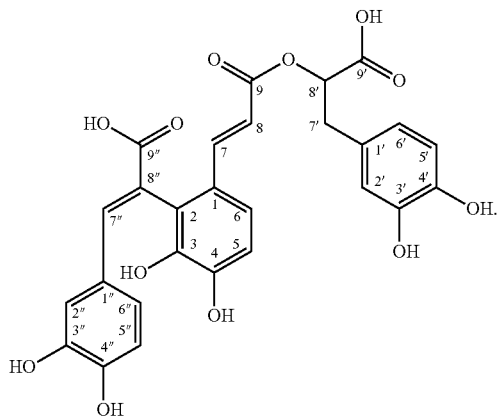

Formula (I)

¹H-NMR shows 1 signal of methenyl proton attached to oxygen at δ 4.93 (1H, dd, 8.0, 4.5 Hz); 11 signals of aromatic proton at δ 6.85 (1H, d, 8.5 Hz), δ 7.31 (1H, d, 8.5 Hz), δ 7.41 (1H, d, 15.5 Hz), δ 6.27 (1H, d, 15.5 Hz), δ 6.62 (1H, s), δ 6.63 (1H, d, 8.0 Hz), δ 6.47 (1H, d, 8.0 Hz), δ 6.44 (1H, d, 2.0 Hz), δ 6.55 (1H, d, 8.5 Hz), δ 6.43 (1H, dd, 8.5, 2.0 Hz), δ 7.69 (1H, s); 2 signals of aliphatic proton at δ 2.89 (2H, ddd, 14.0, 8.0, 4.5 Hz).

Carbon-13 nuclear magnetic resonance ¹³C-NMR spectrum shows 27 carbon signals, including 1 aliphatic carbon signal at δ 36.0, 1 signal of methenyl carbon attached to oxygen at δ 72.8, 3 signals of carbonyl carbon at δ 166.0, δ 170.6, δ 168.4 and 22 signals of double-bond carbon at δ 123.7, δ 126.4, δ 142.9, δ 147.7, δ 115.0, δ 118.4, δ 143.7, δ 113.9, δ 127.1, δ 116.5, δ 143.9, δ 144.8, δ 115.5, δ 120.0, δ 126.0, δ 117.3, δ 144.8, δ 147.2, δ 115.3, δ 122.9, δ 141.1, δ 123.4.

In an embodiment of this invention, said compound of the present invention has 2 isomers with optical rotation respectively at −157.5° and 196.6°. Compound with C-8' absolute configuration set as S/R-configuration is obtained through molecular optimum design and calculated by BPV86 method having TD-SCF with (2d, p) basis sets to read comparison between result and experimental CD spectrum of the compound. It is inferred by the substantially matched CD spectra that the absolute configuration of C-8' in 2 isomers of the compound of the present invention are S configuration and R configuration (see FIG. 10). The spectrum by HMBC of the compound in the present invention is presented as follows:

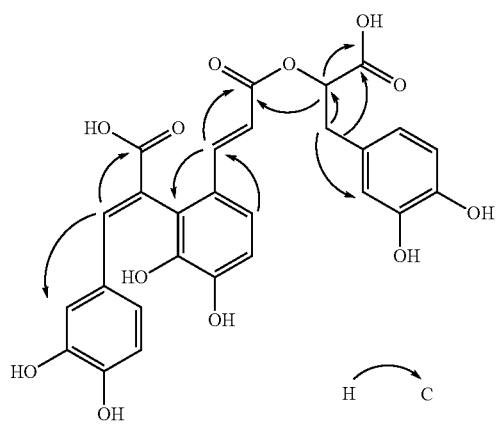

Said salvianolic acid T is prepared by the following method:

a) extraction: extracting Salviae Miltiorrhizae crude drug or a mixture of Salviae Miltiorrhizae and other crude drugs with water and filtering, concentrating the filtrate, adding alcohol to precipitate and obtain a supernatant, then concentrating the supernatant to obtain an extract;

b) separation: dissolving the extract of the step a) in water, applying on the macroporous absorbent resin, eluting the resin with acidic solution to remove the impurities and then eluting with ethanol to obtain an ethanol eluent, concentrating the ethanol eluent to obtain an extract;

c) purification: purifying the extract of the step b) with high-pressure preparative LC; stationary phase is C18 reversed-phase silica column; mobile phase is acetonitrile-water-formic acid by isocratic elution or gradient elution method with detective wavelength at 280 nm; HPLC is used to monitor the process of elution to collect the eluent containing the salvianolic acid T; after being concentrated, the salvianolic acid T is obtained.

In an embodiment of this invention, the preparation of said traditional Chinese medicine composition is provided, and said preparation of the present invention comprises the traditional Chinese medicine composition and one or more kinds of pharmaceutically acceptable carriers. Said traditional Chinese medicine composition may account for 0.1~99.9 wt % of said preparation, and the balanced is pharmaceutically acceptable carrier.

In an embodiment of this invention, the composition is prepared in the form of unit dosage and said unit dosage refers to individual preparation, e.g. each tablet of tablets, each capsule of capsules, each bottle of oral solutions and each bag of granules etc., and is prepared by any one of methods known in pharmaceutical field. All methods include the step of combining traditional Chinese medicine composition with the carriers. Said carriers are composed of one or more kinds of adjuvants. In general speaking, said preparation is prepared by the following method: uniformly and tightly combining said traditional Chinese medicine composition with liquid carrier, finely ground solid carrier or mixture of both to give the outcome, and, if necessary, preparing the outcome into desirable dosage form. Usually, standard pharmaceutical techniques may be used, which includes combining said traditional Chinese medicine composition with pharmaceutically acceptable carrier to prepare them into the pharmaceutical dosage form of the present invention. These methods include steps of mixing, granulating and tableting. Known to the person skilled in the prior art, the form and characteristic of said pharmaceutically acceptable carrier or diluting agent depend on the quantity of bio-active ingredients to be mixed, administration route of preparation and other known factors.

In an embodiment of this invention, said composition can be prepared in any pharmaceutically acceptable dosage form, including the tablet such as sugar-coated tablet, film-coated tablet and enteric-coated tablet, the capsule such as soft capsule and hard capsule, the oral liquid solution, the buccal tablet, the granules, the instant powder, the pill, the pulvis, the paste such as ointment and paster, the Dan, the suspension, the powder, the solution, the injection, the suppository, the cream, the ointment, the plaster, the spray, the drop, the drop pill and the patch, preferably the orally-administrated dosage form, such as the capsule, the tablet, the oral solution, the granule, the pill, the powder, the Dan and the ointment etc.

In an embodiment of this invention, said orally-administrated dosage form includes carriers such as the adhesive, filling agent, diluent, tableting agent, lubricant, disintegrating agent, colorant agent, flavoring agent, wetting agent. If necessary, the tablet may be coated.

In an embodiment of this invention, said filling agents include cellulose, mannitol, lactose and other analogous filling agent. Suitable disintegrating agents include starch, polyvinylpyrrolidone (PVP) and starch derivative (e.g. sodium hydroxyethyl starch). Suitable lubricants include magnesium stearate. Suitable wetting agents include sodium dodecyl sulfate.

In an embodiment of this invention, oral solid preparations of said composition can be prepared by blending repeatedly to make the bio-active ingredients (API) distributed uniformly into a large number of filling agent.

In an embodiment of this invention, oral liquid preparations are in dosage form of either water-soluble or oil-soluble suspension, solution, emulsion, syrup or elixir, or drying powder that is always reconstituted with water or other suitable solvent before clinical use. This liquid preparation may contain conventional excipients, for example suspending agent, e.g. sorbitol, syrup, methylcellulose, gelatin, hydroxy ethyl cellulose, carboxy methyl cellulose, aluminum stearate gel or hydrogenated edible fat; emulsifying-agent, e.g lecithin, sorbitan monoleate or arabic gum; non-aqueous excipient (including edible oil) e.g. almond oil, fractionated coconut oil, oil ester such as glyceride; propylene glycol or ethanol; as well as preservative e.g. methylparaben, nipasol, sorbic acid. If necessary, conventional flavoring agent or colorant agent can be included.

In an embodiment of this invention, said injection contains bio-active components and aseptic excipients. To the person skilled in the prior art, said bio-active component is dissolved or suspended in the liquid according to the type and concentration of excipients. Generally, solution is prepared by dissolving the bio-active components in the excipients, sterilizing, loading into a suitable vial or ampoule and sealing. Some pharmaceutically acceptable adjuvant, e.g. local anaesthetic, preservative and buffering agent can be added as required. In order to improve its stability, before loaded into the vial, this composition of the present invention can be frozen and treated in vacuum to remove water.

In an embodiment of this invention, said traditional Chinese medicine composition can be prepared by optionally adding pharmaceutically acceptable excipients. Said excipients are selected from: mannitol, sorbitol; sodium thiosulfate; cysteine hydrochloride, mercaptoacetic acid, methionine, Vitamin C; EDTA disodium, EDTA calcium disodium salt; monovalent alkali carbonate, acetate, phosphate or its aqueous solution; hydrochloride, acetic acid, sulfuric acid, phosphoric acid; amino acid; sodium chloride, potassium chloride, sodium lactate; xylitol; maltose, glucose, fructose, dextran; glycine; starch, sucrose, lactose, mannitol; silicon derivative; cellulose and its derivatives; alginate; gelatin; PVP, glycerol; Tween-80, agar gel; calcium carbonate, calcium bicarbonate; surfactant; PEG; cyclodextrin; phospholipids; Kaolin; talcum powder, calcium stearate, magnesium stearate; and the like.

Preferably, said composition is prepared into the drop pill, more preferably the micro drop pill.

In an embodiment of this invention, a compound *Salvia* micro drop pill (CSMDP) is provided and said CSMDP is prepared with traditional Chinese medicine composition and the micro drop pill matrix in a ratio of 1:5~5:1 by weight, preferably prepared with traditional Chinese medicine composition and the micro drop pill matrix in a ratio of 1:3~3:1 by weight, most preferably in a ratio of 1:(1~3).

In an embodiment of this invention, the preparation method for preparing CSMDP comprises following steps:

(1) Material melting step: charging the medicine and drop pill matrix into a homogenizer, mixing homogenously at 1000~5000 rpm for 1~200 min, melting homogenously at 3000~10000 rpm for 1~100 min; during the melting process, the temperature is kept at 60~100° C. to obtain the molten medicine liquid; the ratio of the medicine to the micro drop pill matrix is 1:5~5:1 by weight;

(2) Dropping step: delivering the molten medicine liquid to a dripper, and acquiring medicine drops from the dripper by means of vibration dropping at a vibration frequency of 2~2000 Hz under a dropping pressure of 0.5~4.0 Bar, with an acceleration at 1~20 G; and the temperature of the dripper is at 70° C.~300° C.; the dropping rate is matched with the melting rate in step (1); and (3) Condensation step: cooling the medicine drops with cooling gas rapidly to solidify and obtaining solid drop pill having a particle size of 0.2 mm~4.0 mm; the temperature of the cooling gas is 0° C. or lower.

Preferably, the preparation method for preparing CSMDP comprises following steps:

(1) Material melting step: charging the medicine and matrix into a homogenizer, mixing homogenously at 1000~5000 rpm for 1~200 min, melting homogenously at 3000~10000 rpm for 1~100 min; during the melting process, the temperature is kept at 60~100° C. to obtain the molten medicine liquid; the ratio of medicine to the micro drop pill matrix is 1:3~3:1 by weight;

(2) Dropping step: delivering the molten medicine liquid to a dripper, and acquiring medicine drops from the dripper by means of vibration dropping at a vibration frequency of 20~300 Hz under a dropping pressure of 0.5~4.0 Bar, with an acceleration at 1~15 G; the temperature of the dripper is at 70° C.~200° C.; the dropping rate is matched with the melting rate in step (1); and (3) Condensation step: cooling the medicine drops with cooling gas rapidly to solidify and obtaining the solid drop pill having a particle a size of 0.2 mm~4.0 mm; the temperature of the cooling gas is 0° C. or lower.

Wherein, in step (1), said drop pill matrix includes one or more of PEG, sorbitol, xylitol, lactitol, maltose, starch, methylcellulose, sodium carboxymethyl cellulose, hydroxypropyl methylcellulose (HPMC), Arabic gum, alginate, dextrin, cyclodextrin and agar, preferably the solid PEG, e.g. PEG-1000, PEG-2000, PEG-3000, PEG-4000, PEG-5000, PEG-6000, PEG-7000 and PEG-8000, more preferably one or more of the PEG-1000, PEG-2000, PEG-3000, PEG-4000, PEG-6000, PEG-8000, most preferably the PEG-6000, PEG-4000, or the combination of PEG-4000 and PEG-6000. In step (1), homogenization may enhance content uniformity, and RSD is improved from previous 10% to 7%.

Preferably, in step (1), said ratio of medicine to drop pill matrix is 1:3~3:1 by weight, mixing homogeneously 3000~5000 rpm for 10~60 min and melting homogeneously at 4000~9000 rpm for 5~30 min, and during the melting process the temperature is kept at 70~90° C.; most preferably, said ratio of medicine to the matrix is 1:(1~3) by weight, mixing homogeneously 3000~4000 rpm for 10~30 min and melting homogeneously at 4000~6000 rpm for 6~30 min, and during the melting process the temperature is kept at 75~85° C.

In step (2), preferably, said temperature of dripper is at 70~100° C., preferably 75~85° C.; the vibration frequency at 50~300 Hz, preferably 100~200 Hz, more preferably 90~200 Hz, more preferably 130~140 Hz, most preferably 137 Hz; acceleration at 3.5~4.5 G preferably 4.0 G; dropping pressure at 1.0~3.0 Bar, preferably 1.8 Bar; dropping rate is 10~14 Kg/h, preferably 12~30 Kg/h, further preferably 15~25 Kg/h.

In step (3), said condensation by cooling gas means that the falling drops are cooled by using low-temperature condensate trap to make solidification. Said temperature of cooling gas is 0° C. or lower, preferably at 0~−150° C., further preferably −60° C.~−140° C., most preferably −80° C.~−120° C.; said cooling gas is air, nitrogen or inert gas; said particle size of micro drop pill is 1.0 mm~2.0 mm.

Further, said method may additionally comprise step (4) of drying step: fluidized-bed drying equipment is preferred at −20~100° C., preferably drying at −20~90° C. for 1~4 hours to obtain the blank drop pill. Especially, fluidized-bed drying the low-temperature drop pill from step (3) is performed at 40~150° C., preferably 40~60° C. for 1~4 hours, preferably 1~3 hours, most preferably 2 hours, to obtain the blank drop pill.

In step (4), gradient-rising temperature drying method is preferred, including steps of: fluidizing at −20~30° C., drying at 15~35° C. for 10~120 min, drying at 35~55° C. for 10~60 min, drying at 55~100° C. for 0~60 min; preferably fluidizing at 0~20° C., drying at 25° C. for 60 min, drying at 45° C. for 30 min, drying at 55° C. for 0~30 min. In this step, the drop pills are in state of fluidization, not only solving the problems of drop pill adhesion, but also enhancing the efficiency and productivity up to 30 kg/h.

In step (4), by screening through a large number of the drying methods, the inventors found that: in step (3), the blank pill is dried by one of following drying methods: the low-humidity airing method, coating pot drying method, vacuum oven drying method, hot-air blasting drying method, track microwave heating drying method, fluidization drying coating method. In terms of yield and productivity, the coating pot drying method, track microwave heating drying method and fluidization drying coating method are preferred. In terms of the industrialization, the fluidization bed drying method is preferred, and the fluidization drying coating method is more preferred. Advantages and disadvantages of various drying methods are shown in Table 1.

TABLE 1

| No. | Drying mode | Advantages | Disadvantages |
|---|---|---|---|
| 1 | Low-temperature airing | High yield. The yield is usually about 95% without consideration of dropping factors. | (1) Stringent requirement for drying environment, demanding the air-circulated clean workshop with the relative humidity less than 30%, temperature 20° C. or more; (2) Prolonged drying period, 48 hours required when thickness of drop pill is up to about 2 cm; (3) Large area workshop occupied; (4) Turning regularly; (5) Exposing for long time, prone to pollution. |
| 2 | Coating pot drying | (1) High yield. The yield is usually about 95% without consideration of dropping factors; (2) Drying and coating can be achieved simultaneously. | (1) Demanding the inlet air having low humidity, generally not more than 5 g/kg; (2) Low drying efficiency at least 6 h/batch; (3) Customized device; (4) Easily resulting in product rejection due to the adhersion of drop pills. |
| 3 | Vacuum oven drying | None | (1) Low drying efficiency, demanding longtime low-temperature vacuum drying, at least 30 hours/batch; (2) Low-productivity device, the productivity of oven per square meter is difficult to exceed 0.2 kg/h; (3) Easily resulting in adhesion and deformation of drop pill, which is not round in appearance. |
| 4 | Hot-air blasting drying | None | (1) Low drying efficiency, demanding low-temperature drying for long time, at least 40 hours/batch; (2) Low-productivity device, the productivity of oven per square meter is difficult to exceed 0.1 kg/h; (3) Easily resulting in adhesion and deformation of drop pill, which is not round in appearance; (4) Drying workshop with relative humidity of less than 30%. |
| 5 | Track microwave heating drying | High yield, reaching 20 Kg/h. | (1) Difficult to control the drying process, easily resulting in adhesion and deformation of drop pill, which is not round in appearance, or product rejection due to charring; (2) Relative humidity less than 30% in drying workshop; (3) Unable to solve residual microwave in product. |
| 6 | Fluidization driying coating drying | (1) High yield, reaching 30 kg/h; (2) Drying and coating simultaneously; (3) Round drop pill in appearance; (4) High yield. The yield is usually over | Inlet air humidity should be controlled, generally not more than 7.5 g/kg. |

TABLE 1-continued

| No. | Drying mode | Advantages | Disadvantages |
|---|---|---|---|
| | | 98% without consideration of dropping factors; (5) Easily controlled during drying, real-time displaying the water content. | |

Further, said preparation method for micro drop pill may additionally comprise step (5) of coating: coating the blank pill obtained from step (4) in a state of fluidization at 30~65° C.; the concentration of coating liquid is at 5~25 wt %, preferably 18~20 wt %; the coating material is selected from shellac, CAP (cellulose acetate phthalate), methyl acrylate, methyl methacrylate or opadry; the ratio of coating material to the blank pill is 1:50~1:10, preferably 1:50~1:25.

In order to better implement the preparation method for micro drop pill, preferably, said method may additionally comprise a premixing step before step (1): adding the medicine powder or extract with water, stirring over 10 min at 30~80° C. to obtain the premixed material, ensuring the homogenization of water. This step may remedy the defects brought about by inputted dried powder.

In an embodiment of this invention, said micro drop pills prepared by the method may be either packaged directly, or prepared into capsule after loading into capsule shell. After preparation of capsule, the weighing step for capsule may be additionally employed one by one. High-speed weighing for the loaded capsule one-by-one before packaging is employed so as to eliminate possibly substandard capsules.

In an embodiment of this invention, said method is characterized in that: it is the first time to creatively combine the techniques of vibration dropping and air cooling with the fluidization drying coating method to apply to the formulation of drop pill and drop pill capsule. Hence, both producing rate and forming quality of the drop pill are increased, further simplifying the production process. The advantages of the present invention are presented as follows:

1. Using method of vibration dropping and air cooling instead of traditional drop pill preparation method (gravity/pressure dropping and coolant cooling)

Utilization of air cooling well met the requirements of high-speed dropping, preparing a micro drop pill (with the particle size of 2.5 mm or smaller) and increasing drug-loading capacity. As a result of this, the drug-loading capacity of drop pill had been increased exponentially and the amount and dose of the drop pill matrix reduced dramatically. Moreover, the productivity of the drop pills had been enhanced greatly from traditional rate of 1~2 pills/s to 1000~1250 pills/s, and the particle size ranged from 2 mm~4 mm to 0.2 mm~4 mm. It was possible to produce the micro drop pills that could be loaded into the capsule. By adjusting the vibration parameters and fluidization coating, the drug-loading capacity would be increased from about 25% traditionally to about 50% or more, and therefore the amount of matrix reduced by leaps and bounds.

2. Lowered cost: instead of the traditional coolant of liquid paraffin and silicone oil etc, the low-temperature air, nitrogen or inert gas were employed to perform cooling, avoiding follow-up steps of eliminating residual solvent (e.g. step of removing oil). Hence, the operation process was simplified and totally free of residual organic solvent. The preparation cost was lowered.

3. The fluidization drying was added, which might not only prevent the drop pill from adhesion, precipitation of constituents and reduced volatile oil caused by the storage stage of air cooling method, but also reduce drying time (from 4~24 hours to 2 hours). By using fluidization coating, the molten medicine liquid was injected to coat with drug-loading, further improving the drug-loading capacity. Also, this technique of injection was used for coating the drop pills so as to realize the purposes of different techniques (e.g. the sustained release coating, film coating and sugar coating etc). Because the fluidization was believed to be a mild process, it not only ensured the water to reach a stable value, but also improved the drug-loading capacity and the uniformity of coating in the drop pills. Unlike the drop pills prepared by the traditional methods, the fluidization would prevent the drop pills from being cleft and white-dotted and at same time, the yield was increased.

Comparison of the physic-chemical parameters between the micro drop pill of the present invention (CSDP prepared by the method of Example 15) and traditional drop pill was presented in Table 2.

TABLE 2

| | Micro drop pill in the present invention | Commercially available drop pills |
|---|---|---|
| Weight & volume | Smaller weight, about 4 mg, so as to be accurately filled into capsule | Larger weight, 25 mg~27 mg |
| Drug-loading capacity | Drug-loading 30 wt % (calculated based on dried extract) | Drug-loading 18~20 wt % (calculated based on dried extract) |
| Appearance | Replacing the original cooling liquid with air cooling, ensuring condensation forming effect, overcoming the drawbacks of residual cooling liquids | Residual cooling liquids on the surface of drop pill |
| Efficiency | Super high-speed vibration and pressurized dropping ensuring a stable delivery of materials, | Slower dropping rate than the vibration dropping, complicated process of eliminating the cooling |

TABLE 2-continued

|  | Micro drop pill in the present invention | Commercially available drop pills |
| --- | --- | --- |
| Release rate | increasing dropping rate, greatly improving the efficiency Totally mixing the medicine with the matrix by homogenizer, dispersing the medicine active ingredients, helping drug absorption, reducing the pill weight so as to not only be accurately filled into capsule, but also quicken drug release, enhancing clinical efficacy | liquids on the surface, requiring long time — |
| Roundness & particle size | Excellent roundness, the particle size of 1 mm~2 mm, capable of preparing drop pills having a particle size of 0.2 mm~4 mm | Good roundness, particle size of 3 mm~4 mm, unable to reach 1 mm~2 mm |

EXAMPLES

The following examples are offered for purposes of elaborating explanation of the present invention only and are not intended to limit the scope of the invention in any way.

Determination Method of *Salvia Miltiorrhiza* and *Panax Notoginseng* Extract

In following Examples, each ingredient of the traditional Chinese medicine was determined by following method, including the Danshensu, Salvianolic acid T, protocatechuic aldehyde, Salvianolic acid D, rosmarinic acid, Salvianolic acid B, Salvianolic acid A, dihydrotanshinone I, tanshinone I, cryptotanshinone, tanshinone IIA, *Panax Notoginseng* Saponin R1, Ginsenoside Rg1, Ginsenoside Re, Ginsenoside Rb1 and Ginsenoside Rd.

Determination of Salvianolic Acids and Tanshinones

Preparation of Reference and Tested Solutions

Preparation of reference solution: a certain amount of reference substances, including the Danshensu, Salvianolic acid T, protocatechuic aldehyde, Salvianolic acid D, rosmarinic acid, Salvianolic acid B, Salvianolic acid A, dihydrotanshinone I, tanshinone I, cryptotanshinone, tanshinone IIA, were weighed accurately, transferred to 10 ml volumetric flask and diluted with methanol to the scale, which was continued to be diluted as required, shook well and filtered through 0.22 μm membrane to give the reference solution respectively as follows: Danshensu at 0.0315 mg/ml, Salvianolic acid T at 0.04596 mg/ml, protocatechuic aldehyde at 0.07556 mg/ml, Salvianolic acid D at 0.04385 mg/ml, rosmarinic acid at 0.04263 mg/ml, Salvianolic acid B at 0.04248 mg/ml, Salvianolic acid A at 0.1118 mg/ml, dihydrotanshinone I at 0.02098 mg/ml, tanshinone I at 0.02085 mg/ml, cryptotanshinone at 0.02442 mg/ml, tanshinone IIA at 0.01992 mg/ml.

Preparation of tested solution: 0.1 g of *Salvia Miltiorrhiza* and *Panax Notoginseng* extract was weighed accurately, transferred to 10 ml volumetric flask, dissolved with purified water, diluted to scale and filtered through 0.22 μm membrane to give the tested solution.

Method: 10 μl of reference and tested solutions were respectively absorbed with precision and injected into HPLC to assay.

Chromatographic column: Agilent Zorbax SB C18 (4.6× 250 mm, 5 μm);
Flow rate: 0.5 mL/min
Column temperature: 30° C.
Detective wavelength: 281 nm,
The eluting condition was presented in following Table 3.

TABLE 3

| Time (min) | A (%) Water (0.02% formic acid) | B (%) Acetonitrile (0.02% formic acid) |
| --- | --- | --- |
| 0 | 90 | 10 |
| 15 | 80 | 20 |
| 25 | 75 | 25 |
| 30 | 74 | 26 |
| 45 | 54 | 46 |
| 50 | 48 | 52 |
| 62 | 28 | 72 |
| 70 | 0 | 100 |
| 76 | 0 | 100 |

Figure 11:
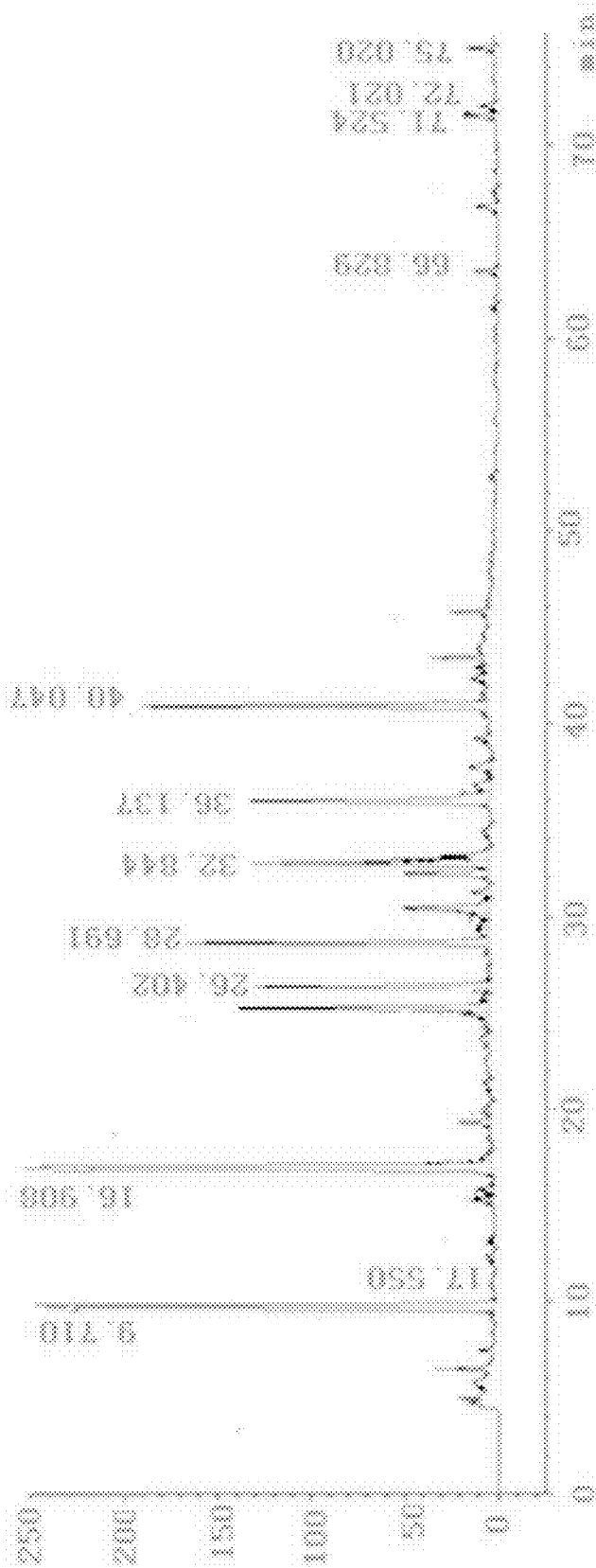
FIG. 11 was the chromatogram of Salvianolic acids and tanshinones (detective wavelength at 281 nm).

Wherein, the retention time of Danshensu, Salvianolic acid T, protocatechuic aldehyde, Salvianolic acid D, rosmarinic acid, Salvianolic acid B, Salvianolic acid A, dihydrotanshinone I, tanshinone I, cryptotanshinone and tanshinone IIA under wavelength of 281 nm was presented in FIG. 11 and Table 4.

TABLE 4

| Grouping of ingredients | Retention time (min) | Peak name |
| --- | --- | --- |
| Salvianolic acids | 9.710 | Danshensu |
|  | 16.908 | protocatechuic aldehyde |
|  | 26.402 | Salvianolic acid T |
|  | 28.691 | Salvianolic acid D |
|  | 32.844 | rosmarinic acid |
|  | 36.137 | Salvianolic acid B |
|  | 40.047 | Salvianolic acid A |
| Tanshinones | 66.829 | dihydrotanshinone I |
|  | 71.524 | tanshinone I |
|  | 72.021 | Cryptotanshinone |
|  | 75.020 | tanshinone IIA |

Determination of Saponins

Preparation of reference solution: a certain amount of reference substances, including the *Panax Notoginseng* Saponin R1, Ginsenoside Rg1, Ginsenoside Re, Ginsenoside Rb1 and Ginsenoside Rd, were weighed accurately, into which methanol was added to give the reference solution, respectively containing 0.5 mg, 2.0 mg, 1.0 mg, 0.5 mg, 0.5 mg, 0.5 mg, 1.0 mg per ml.

Preparation of tested solution: 0.1 g of *Salvia Miltiorrhiza* and *Panax Notoginseng* extract was weighed accurately, dissolved with 4% ammonia solution (10 ml) and passed through D101 macro porous column (inner diameter: 0.7 cm and height: 5 cm), which was eluted firstly with 30 ml water, 30 ml methanol (30%) and 10 ml methanol to collect the methanol solution in 10 volumetric flask, shake well to give the tested solution.

Chromatographic condition and system suitability test: octadecylsilane bonded silica gel was used as bulking agent; acetonitrile was used as mobile phase "A" and water as mobile phase "B". According to following Table 5, a gradient elution method was used, and flow rate was at 1.0 ml/min, detective wavelength at 203 nm, column temperature at 30° C. and recording time 75 min.

TABLE 5

| mobile phase of gradient elution | | |
|---|---|---|
| Time (min) | Mobile phase A | Mobile phase B |
| 0 | 20 | 80 |
| 25 | 25 | 75 |
| 60 | 40 | 60 |
| 70 | 70 | 30 |
| 75 | 20 | 80 |
| 80 | 20 | 80 |

Figure 12:
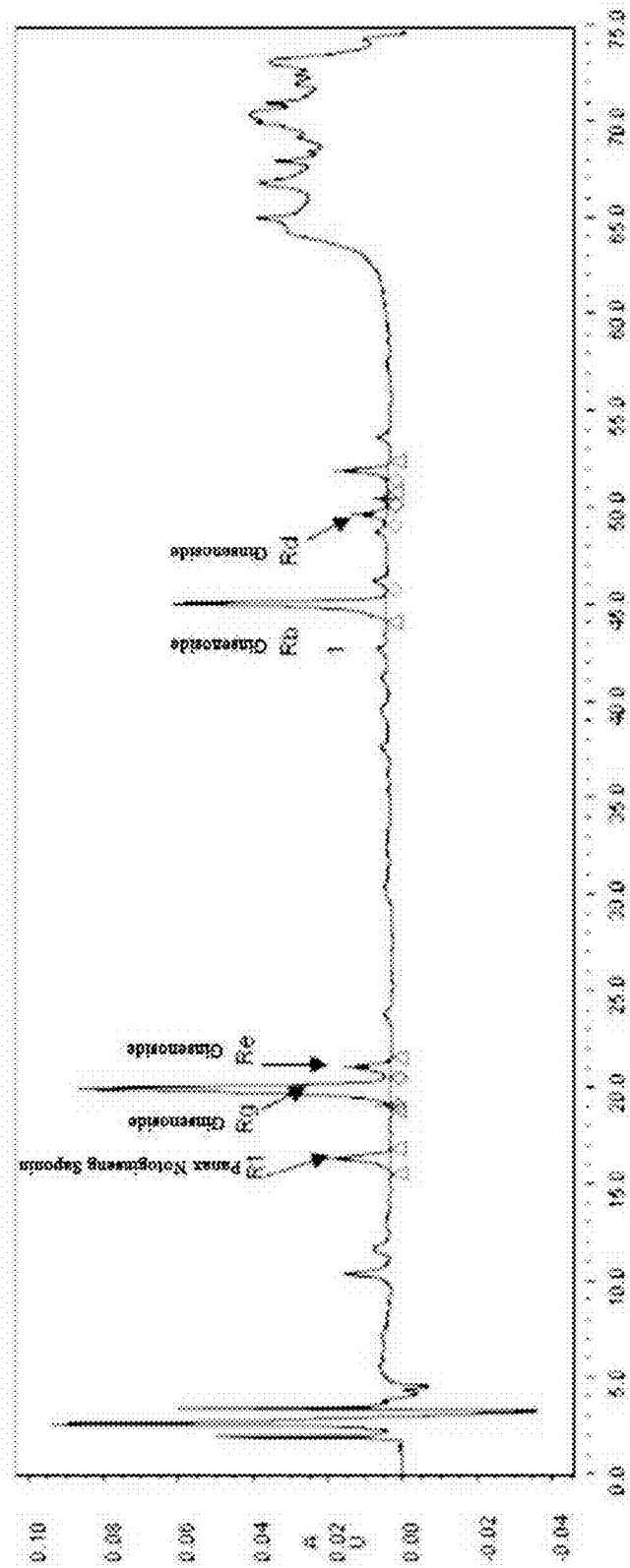
FIG. 12 was the chromatogram of saponines.

Measurement: 10 μl of reference and tested solutions were respectively absorbed with precision and injected into HPLC to assay under aforesaid conditions. The retention time of each ingredient was presented in FIG. 12.

Preparation of Traditional Chinese Medicine Composition of the Present Invention Example 1

820 g of crude medicine of *Salvia Miltiorrhiza* was cut into the pieces of 1~2 cm in length and 160 g of crude medicine of *Panax Notoginseng* ground into particles of 0.18 cm. Sodium bicarbonate accounting for 2.25 wt % of total crude medicine was weighed and charged into an extracting tank together with *Salvia Miltiorrhiza* and *Panax Notoginseng* and 5 times of water was added to heat and keep boiling for 2 h and filtered. Resultant residues were extracted for $2^{nd}$ time by adding with 4 times of water to heat and keep boiling for 2 h and filtered. The residues were removed. The extraction solution obtained by two extractions was concentrated to a relative density of 1.16-1.20 (80±5° C.) or a relative sugar degree of 48~52% to give the concentrated liquid. The liquid was delivered to the alcohol precipitation tank, into which a proper amount of ethanol was poured to make final ethanol content of 65~70% and allowed to stand still for 12 hours to precipitate completely. The supernatant was separated and the deposit eliminated. The supernatant was concentrated to give the extract, which was dried to obtain *Salvia Miltiorrhiza* and *Panax Notoginseng* extract.

By aforesaid method, the *Salvia Miltiorrhiza* and *Panax Notoginseng* extract was determined and the concentration of ingredients was presented as follows: the Danshensu at 36 mg/g, Salvianolic acid T at 1 mg/g, protocatechuic aldehyde at 17 mg/g, Salvianolic acid D at 6 mg/g, rosmarinic acid at 7 mg/g, Salvianolic acid B at 13 mg/g, Salvianolic acid A at 9 mg/g, *Panax Notoginseng* Saponin R1 at 17 mg/g, Ginsenoside Rg1 at 24 mg/g, Ginsenoside Re at 3 mg/g, Ginsenoside Rb1 at 18 mg/g and Ginsenoside Rd at 4 mg/g, dihydrotanshinone I at 0.3 mg/g, tanshinone I 0.7 mg/g, cryptotanshinone at 0.6 mg/g, tanshinone IIA at 2.7 mg/g.

90 g of the *Salvia Miltiorrhiza* and *Panax Notoginseng* extract was added with 9 g of borneol to give the traditional Chinese medicine.

Example 2

75 g of *Salvia Miltiorrhiza* and *Panax Notoginseng* extract obtained from Example 1 and 25 g of borneol was mixed uniformly to give the traditional Chinese medicine composition.

Example 3

800.0 g of crude medicine of *Salvia Miltiorrhiza* and 150.0 g of *Panax Notoginseng* were decocted with water under alkaline condition for 3 times (pH=9), 1 hour each time and filtered to give filtrate I. Resultant residue was decocted with water for 3 times, 1 hour each time and filtered to give the filtrate II. Filtrate I and filtrate II were combined and concentrated. The concentrated liquid was added with ethanol to make final ethanol content of 70% and allowed to stand still. The supernatant was filtered to recover the ethanol, which was concentrated and dried to obtain *Salvia Miltiorrhiza* and *Panax Notoginseng* extract.

By aforesaid method, the *Salvia Miltiorrhiza* and *Panax Notoginseng* extract was determined and the concentration of ingredients was presented as follows: the Danshensu at 40 mg/g, Salvianolic acid T at 12 mg/g, protocatechuic aldehyde at 20 mg/g, Salvianolic acid D at 7 mg/g, rosmarinic acid at 9 mg/g, Salvianolic acid B at 16 mg/g, Salvianolic acid A at 12 mg/g, *Panax Notoginseng* Saponin R1 at 9 mg/g, Ginsenoside Rg1 at 28 mg/g, Ginsenoside Re at 4 mg/g, Ginsenoside Rb1 at 22 mg/g and Ginsenoside Rd at 6 mg/g, dihydrotanshinone I at 0.4 mg/g, tanshinone I 0.8 mg/g, cryptotanshinone at 0.6 mg/g, tanshinone IIA at 2.8 mg/g.

99.9 g of the *Salvia Miltiorrhiza* and *Panax Notoginseng* extract was added with 0.1 g of borneol to give the traditional Chinese medicine.

Example 4

90 g of *Salvia Miltiorrhiza* and *Panax Notoginseng* extract obtained from Example 3 and 10 g of borneol was mixed uniformly to give the traditional Chinese medicine composition.

Example 5

750 g of crude medicine of *Salvia Miltiorrhiza* and 250 g of *Panax Notoginseng* were decocted with water under alkaline condition for 2 times (pH=7.5), 2 hours each time and filtered to give filtrate I. Resultant residue was decocted with water for 2 times, 2 hours each time and filtered to give the filtrate II. Filtrate I and filtrate II were combined and concentrated. The concentrated liquid was added with ethanol to make final ethanol content of 70% and allowed to stand still. The supernatant was filtered to recover the ethanol, which was concentrated and dried to obtain *Salvia Miltiorrhiza* and *Panax Notoginseng* extract.

By aforesaid method, the *Salvia Miltiorrhiza* and *Panax Notoginseng* extract contained the Danshensu, Salvianolic acid T, protocatechuic aldehyde, Salvianolic acid D, rosmarinic acid, Salvianolic acid B, Salvianolic acid A, *Panax Notoginseng* Saponin R1, Ginsenoside Rg1, Ginsenoside Re, Ginsenoside Rb1, Ginsenoside Rd dihydrotanshinone I, tanshinone I, cryptotanshinone and tanshinone IIA respectively at 30 mg/g, 9 mg/g, 14 mg/g, 5 mg/g, 10 mg/g, 7 mg/g, 5 mg/g, 18 mg/g, 2 mg/g, 17 mg/g, 2 mg/g, 0.3 mg/g, 0.7 mg/g, 0.5 mg/g and 2.6 mg/g.

50 g of the *Salvia Miltiorrhiza* and *Panax Notoginseng* extract was added with 50 g of borneol to give the traditional Chinese medicine.

Example 6

99 g of *Salvia Miltiorrhiza* and *Panax Notoginseng* extract obtained from Example 5 and 1 g of borneol was mixed uniformly to give the traditional Chinese medicine composition.

Example 7

83 weight parts of *Salvia Miltiorrhiza* and 17 weight parts of *Panax Notoginseng* were decocted with water under alkaline condition for 2 times (pH=7.5), 2 hours each time and filtered to give filtrate I. Resultant residue was decocted with water for 2 times, 2 hours each time and filtered to give the filtrate II. Filtrate I and filtrate II were combined and concentrated. The concentrated liquid was added with ethanol to make final ethanol content of 70% and allowed to stand still. The supernatant was filtered to recover the ethanol, which was concentrated and dried to obtain *Salvia Miltiorrhiza* and *Panax Notoginseng* extract. 1 weight part of borneol was added to give the traditional Chinese medicine. Said borneol was commercially available.

By aforesaid method, the *Salvia Miltiorrhiza* and *Panax Notoginseng* extract contained the Danshensu, Salvianolic acid T, protocatechuic aldehyde, Salvianolic acid D, rosmarinic acid, Salvianolic acid B, Salvianolic acid A, *Panax Notoginseng* Saponin R1, Ginsenoside Rg1, Ginsenoside Re, Ginsenoside Rb1, Ginsenoside Rd dihydrotanshinone I, tanshinone I, cryptotanshinone and tanshinone IIA respectively at 40 mg/g, 12 mg/g, 20 mg/g, 7 mg/g, 9 mg/g, 16 mg/g, 12 mg/g, 9 mg/g, 28 mg/g, 4 mg/g, 22 mg/g, 6 mg/g, 0.4 mg/g, 0.8 mg/g, 0.6 mg/g, 2.8 mg/g.

Example 8

400 g of crude medicine of *Salvia Miltiorrhiza* was cut into the pieces of 1~2 cm in length and 80 g of crude medicine of *Panax Notoginseng* ground into particles. Sodium bicarbonate accounting for 3 wt % of total crude medicine was weighed and charged into an extracting tank together with *Salvia Miltiorrhiza* and *Panax Notoginseng* and 5 times of water was added to heat and keep boiling for 2 h±20 min and filtered. Resultant residues were extracted for $2^{nd}$ time by adding with 4 times of water to heat and keep boiling for 1 h±15 min and filtered. The residues were removed. The extraction solution obtained by two extractions was concentrated to a relative density of 1.16-1.20 (80±5° C.) or a relative sugar degree of 50% to give the concentrated liquid. The liquid was delivered to the alcohol precipitation tank, into which a proper amount of ethanol was poured to make final ethanol content of 68% and allowed to stand still for 20 hours to precipitate completely. The supernatant was separated and the deposit eliminated. The supernatant was concentrated to give the extract, which was dried to obtain *Salvia Miltiorrhiza* and *Panax Notoginseng* extract.

By aforesaid method, the *Salvia Miltiorrhiza* and *Panax Notoginseng* extract contained the Danshensu, Salvianolic acid T, protocatechuic aldehyde, Salvianolic acid D, rosmarinic acid, Salvianolic acid B, Salvianolic acid A, *Panax Notoginseng* Saponin R1, Ginsenoside Rg1, Ginsenoside Re, Ginsenoside Rb1, Ginsenoside Rd dihydrotanshinone I, tanshinone I, cryptotanshinone and tanshinone IIA respectively at 20 mg/g, 5 mg/g, 10 mg/g, 2 mg/g, 0.2 mg/g, 5 mg/g, 5 mg/g, 2 mg/g, 1 mg/g, 1 mg/g, 10 mg/g, 1 mg/g, 0.1 mg/g, 0.5 mg/g, 0.2 mg/g, 1 mg/g.

90 g of the *Salvia Miltiorrhiza* and *Panax Notoginseng* extract was added with 9 g of borneol to give the traditional Chinese medicine.

Example 9

500 g of crude medicine of *Salvia Miltiorrhiza* was cut into the pieces of 1~2 cm in length and 102 g of crude medicine of *Panax Notoginseng* ground into particles. Sodium bicarbonate accounting for 2.5 wt % of total crude medicine was weighed and charged into an extracting tank together with *Salvia Miltiorrhiza* and *Panax Notoginseng* and 6 times of water was added to heat and keep boiling for 2 h and filtered. Resultant residues were extracted for $2^{nd}$ time by adding with 6 times of water to heat and keep boiling for 1 h and filtered. The residues were removed. The extraction solution obtained by two extractions was concentrated to a relative density of 1.16-1.20 (80±5° C.) or a relative sugar degree of 48% to give the concentrated liquid. The liquid was delivered to the alcohol precipitation tank, into which a proper amount of ethanol was poured to make final ethanol content of 65% and allowed to stand still for 24 hours to precipitate completely. The supernatant was separated and the deposit eliminated. The supernatant was concentrated to give the extract, which was dried to obtain *Salvia Miltiorrhiza* and *Panax Notoginseng* extract.

By aforesaid method, the *Salvia Miltiorrhiza* and *Panax Notoginseng* extract contained the Danshensu, Salvianolic acid T, protocatechuic aldehyde, Salvianolic acid D, rosmarinic acid, Salvianolic acid B, Salvianolic acid A, *Panax Notoginseng* Saponin R1, Ginsenoside Rg1, Ginsenoside Re, Ginsenoside Rb1, Ginsenoside Rd dihydrotanshinone I, tanshinone I, cryptotanshinone and tanshinone IIA respectively at 60 mg/g, 20 mg/g, 30 mg/g, 10 mg/g, 10 mg/g, 20 mg/g, 20 mg/g, 10 mg/g, 40 mg/g, 5 mg/g, 40 mg/g, 10 mg/g, 0.5 mg/g, 1 mg/g, 1 mg/g, 5 mg/g.

99.9 g of the *Salvia Miltiorrhiza* and *Panax Notoginseng* extract was mixed uniformly with 0.1 g of borneol to give the traditional Chinese medicine.

Preparation of Traditional Chinese Medicine Preparation

Example 10

0.5 g of traditional Chinese medicine composition prepared by any one method of Examples 1~9 was mixed uniformly with 10.5 g of PEG-6000, molten by heating and delivered to the dropping machine to acquire medicine drops by means of dropping the medicine solution into liquid paraffin at 6~8° C. Residual liquid paraffin was removed to give 400 micro drop pills.

Example 11

0.5 g of traditional Chinese medicine composition prepared by any one method of Examples 1~9, 4.5 g of glucose, 0.9 g of sodium thiosulphate and 1 ml of distilled water were mixed uniformly to give 500 injectable lyophilized powders by lyophilizing.

Example 12

0.5 g of traditional Chinese medicine composition prepared by any one method of Examples 1~9, 5.5 g of mannitol, 0.9 g of EDTA calcium disodium and 2 ml of distilled water were mixed uniformly to give 300 injectable lyophilized powders by lyophilizing.

Example 13

0.5 g of traditional Chinese medicine composition prepared by any one method of Examples 1~9, 50 g of starch and 50 g of sucrose were mixed uniformly to give the tablets by compression after granulating.

Example 14

0.5 g of traditional Chinese medicine composition prepared by any one method of Examples 1~9, 50 g of starch and 50 g of sucrose were mixed uniformly to give the capsules by filling into capsules.

Preparation of the Micro Drop Pill

Example 15

82.5 g of traditional Chinese medicine composition prepared by the method of Example 1 and 165 g of PEG-6000 were prepared.

(1) Pre-mixing step: the traditional Chinese medicine composition was added with water to pre-mix, stirred in the soaking tank at 40±10° C. over 60 min to make the water content of the composition at 13.0 wt % to give the pre-mixed material for later use;

(2) Melting step: PEG-6000 was firstly input into the melting tank, pre-molten by heating to 90° C., into which the pre-mixed material was added and the resultant liquid was mixed by low-speed homogenization (3200 rpm); after mixing, the homogenization rate was increased to 5000 rpm to melt for 6 min; during the melting process, temperature of the liquid was kept at 80±5° C. to give the molten medicine liquid;

(3) Dropping step: aforesaid molten medicine liquid was delivered to the dripper, the vibration frequency of dripper adjusted to 137 Hz and temperature of dripper adjusted to 80° C.; the liquid was delivered to the dripper under pressure (1.8 Bar), from which the liquid was dropped down by means of vibration; said dropping rate was matched with the melting rate in step (1); and (4) Condensation step: the drops were cooled in cooling duct with the low-temperature inert gas at −115±5° C. to cool the liquid to form the solid drop pill;

(5) Drying step: resultant drop pill was fluidization dried; until the drop pill reached better fluidization state, the temperature was increased to 25° C. to dry for 60 min, continuously increased to 55° C. to dry for 30 min, and deceased to 30° C. or lower to discharge to give the intermediate blank drop pill with the water content controlled in the range of 3.0~7.0 wt %;

(6) Coating step: the amount of coating powder was calculated based on coating feed capacity and formula; Opadry accounting for 4 wt % of the blank drop pill was used to prepare the 18 wt % coating solution and stirred for 45 min; inlet air temperature was initially set to 25° C.; after the standard blank drop pills were loaded into the fluidized bed, the inlet air temperature was increased to 48° C.; until the temperature of the drop pill grew to 38° C., the coating was started; the temperature was kept in the range of 35~45° C. during the coating and decreased to 30° C. or lower after coating; the pills were discharged, screened to get the intermediate coating the drop pills with the coating weight of 3.3±0.7% and the water content in the range of 3.0~7.0 wt %.

(7) Loading into capsule and packaging step: the resultant micro drop pills with the particle size of 1.0 mm~2.0 mm were loaded into the capsules; 100% of capsules were on-line checkweighed with a capsule checkweigher, packaged to give the final product.

Wherein, during the process of dropping, formation of drop pill was measured visually by using stroboscopic illumination to perform real-time monitoring and adjustment. In order to improve the uniformity and roundness of the drop pills, the step of screening and regulating might be added.

Example 16

Except that the ratio of traditional Chinese medicine composition to PEG-6000 was 1:5, the CSMDP was prepared by the method of Example 15.

Example 17

Except that the ratio of traditional Chinese medicine composition to PEG-6000 was 5:1, the CSMDP was prepared by the method of Example 15.

Example 18

Following materials were taken: 82.5 g of traditional Chinese medicine composition prepared by Example 1 and 165 g of a mixture of cyclodextrin and agar (1:1). CSMDP was prepared according to the following method:

(1) Melting step: the mixture of cyclodextrin and agar (1:1) was used as a matrix, charged into the homogenizer with the traditional Chinese medicine composition to homogenize at 1000 rpm for 1 min to give the material; the material was molten at 3000 rpm for 1 min; during the melting process, the temperature was kept at 60° C. to obtain the molten medicine liquid;

(2) Dropping step: the molten medicine liquid was delivered to a dripper and dropped by means of vibration dropping at dripper temperature of 70° C. at a vibration frequency of 50 Hz under a dropping pressure of 0.5 Bar; said dropping rate was matched with the melting rate in step (1); and (3) Condensation step: the medicine drops were cooled with cooling gas rapidly to solidify to obtain the blank drop pill having a particle size of 0.2 mm; said temperature of cooling gas was 0° C.

Example 19

Following materials were taken: 82.5 g of traditional Chinese medicine composition prepared by Example 1 and 165 g of a mixture of Arabic gum and lactose (1:1). CSMDP was prepared according to the following method:

(1) Melting step: the mixture of Arabic gum and lactose (1:1) was used as a matrix, charged into the homogenizer with the traditional Chinese medicine composition to homogenize at 5000 rpm for 200 min to give the material; the material was molten at 10000 rpm for 100 min; during the melting process, the temperature was kept at 100° C. to obtain the molten medicine liquid;

(2) Dropping step: the molten medicine liquid was delivered to a dripper and dropped by means of vibration dropping at dripper temperature of 300° C. at a vibration frequency of 300 Hz under a dropping pressure of 4.0 Bar; said dropping rate was matched with the melting rate in step (1); and (3) Condensation step: the medicine drops were cooled with cooling gas rapidly to solidify to obtain the blank drop pill having a particle size of 4.0 mm; said temperature of cooling gas was −150° C.

Example 20

Following materials were taken: 82.5 g of traditional Chinese medicine composition prepared by Example 1 and 165 g of lactitol. CSMDP was prepared according to the following method:

(1) Melting step: the lactitol was used as a matrix, charged into the homogenizer with the traditional Chinese medicine composition to homogenize at 2500 rpm for 100 min to give the material; the material was molten at 6000 rpm for 50 min; during the melting process, the temperature was kept at 80° C. to obtain the molten medicine liquid;

(2) Dropping step: the molten medicine liquid was delivered to a dripper and dropped by means of vibration dropping at dripper temperature of 150° C. at a vibration frequency of 150 Hz under a dropping pressure of 2 Bar; said dropping rate was matched with the melting rate in step (1); and (3) Condensation step: the medicine drops were cooled with cooling gas rapidly to solidify to obtain the blank drop pill having a particle size of 2 mm; said temperature of cooling gas was −100° C.;

(4) Drying step: resultant drop pill was fluidization dried at 50° C. for 2 hours to give the dried blank drop pill;

(5) Coating step: resultant dried blank drop pills were coated at 40° C. in fluidized bed to obtain coated drop pill; said ratio of coating material to the dried blank pills was 1:25; the concentration of said coating solution was 10 wt % and said coating material was Opadry.

Example 21

Following materials were taken: 82.5 g of traditional Chinese medicine composition and 165 g of PEG-8000. CSMDP was prepared according to the following method:

Said traditional Chinese medicine composition powder was added with water and stirred at 60° C. for 10 min or more to obtain the pre-mixed traditional Chinese medicine composition.

(1) Melting step: the PEG-8000 and said pre-mixed traditional Chinese medicine composition were charged into the homogenizer to mix at 2500 rpm for 100 min to give the material; the material was molten homogenizedly at 6000 rpm for 50 min; during the melting process, the temperature was kept at 80° C. to obtain the molten medicine liquid;

(2) Dropping step: the molten medicine liquid was delivered to a dripper and dropped by means of vibration dropping at dripper temperature of 150° C. at a vibration frequency of 150 Hz under a dropping pressure of 2 Bar; said dropping rate was matched with the melting rate in step (1); and (3) Condensation step: the medicine drops were cooled with cooling gas rapidly to solidify to obtain the blank drop pill having a particle size of 2 mm; said temperature of cooling gas was −100° C.;

(4) Drying step: resultant drop pill was fluidization dried at 50° C. for 2 hours to give the dried blank drop pill;

(5) Coating step: resultant dried blank drop pills were coated at 40° C. in fluidized bed to obtain coated drop pill; said ratio of coating material to the dried blank pills was 1:25; the concentration of said coating solution was 10 wt % and said coating material was shellac.

Example 22

Following materials were taken: 92 g of traditional Chinese medicine composition and 270 g of PEG-1000. CSMDP was prepared according to the following method:

Said traditional Chinese medicine composition powder was added with water and stirred at 30° C. for 10 min or more to obtain the pre-mixed traditional Chinese medicine composition.

(1) Melting step: the PEG-1000 and said pre-mixed traditional Chinese medicine composition were charged into the homogenizer to mix at 2500 rpm for 100 min to give the material; the material was molten homogenizedly at 6000 rpm for 20 min; during the melting process, the temperature was kept at 100° C. to obtain the molten medicine liquid;

(2) Dropping step: the molten medicine liquid was delivered to a dripper and dropped by means of vibration dropping at dripper temperature of 70° C. at a vibration frequency of 100 Hz under a dropping pressure of 1.0 Bar; acceleration at 1 G and dropping rate at 10 Kg/h; said dropping rate was matched with the melting rate in step (1); and (3) Condensation step: the medicine drops were cooled with cooling gas rapidly to solidify to obtain the blank drop pill having a particle size of 2 mm; said temperature of cooling gas was −80° C.;

(4) Drying step: resultant drop pill was dried by gradient-rising temperature drying method, fluidized at −20° C., dried at 15° C. for 10 min, 35° C. for 10 min and at 55° C. for 30 min to give the dried blank drop pill;

(5) Coating step: resultant dried blank pills were coated at 40° C. in fluidized bed to obtain coated drop pill; said ratio of coating material to the dried blank pills was 1:25; the concentration of said coating solution was 10 wt % and said coating material was CAP.

Example 23

Following materials were taken: 105 g of traditional Chinese medicine composition and 35 g of a mixture of PEG-4000:PEG-6000 (1:1). CSMDP was prepared according to the following method:

Said traditional Chinese medicine composition powder was added with water and stirred at 80° C. for 10 min or more to obtain the pre-mixed traditional Chinese medicine composition.

(1) Melting step: the mixture of PEG-4000:PEG-6000 (1:1) and said pre-mixed traditional Chinese medicine composition were charged into the homogenizer to mix at 2500 rpm for 100 min to give the material; the material was molten homogenizedly at 6000 rpm for 80 min; during the melting process, the temperature was kept at 80° C. to obtain the molten medicine liquid;

(2) Dropping step: the molten medicine liquid was delivered to a dripper and dropped by means of vibration dropping at dripper temperature of 100° C. at a vibration frequency of 200 Hz under a dropping pressure of 3.0 Bar; acceleration at 20 G and dropping rate at 40 Kg/h; said dropping rate was matched with the melting rate in step (1); and (3) Condensation step: the medicine drops were cooled with cooling gas rapidly to solidify to obtain the blank drop pill having a particle size of 2 mm; said temperature of cooling gas was −120° C.;

(4) Drying step: resultant drop pill was dried by gradient-rising temperature drying method, fluidized at 30° C., dried at 35° C. for 120 min, at 55° C. for 60 min and at 100° C. for 60 min to give the dried blank drop pill;

(5) Coating step: resultant dried blank pills were coated at 35° C. in fluidized bed to obtain coated drop pill; said ratio of coating material to the dried blank pills was 1:25; the concentration of said coating solution was 10 wt % and said coating material was methyl acrylate.

Example 24

Following materials were taken: 600 g of traditional Chinese medicine composition prepared by Example 1, 5 g of borneol and 600 g of xylitol as drop pill matrix.

(1) Melting step: the xylitol was firstly charged into the melting tank and heated to 90° C. to pre-melt, into which said pre-mixed traditional Chinese medicine composition was charged to mix to give the molten medicine liquid;

(2) Dropping step: under pressure the molten medicine liquid was delivered to a dripper that was heated and preserved by steam jacket; at dripper temperature of 40° C. and a vibration frequency of 50 Hz, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −20° C.;

(4) Drying & coating step: resultant solid drop pill was fluidization dried and drug-loading coated to give the coated micro drop pill with the particle size of 0.2 mm~1.0 mm; said drying temperature was 75° C.; and (5) Packaging step: said micro drop pills with the particle size of 0.2 mm~1.0 mm were loaded into the capsules; 100% of capsules were on-line checkweighed with a capsule checkweigher and packaged to give the final product.

Wherein, during the process of dropping, formation of drop pill was measured visually by using stroboscopic illumination to perform real-time monitoring and adjustment. In order to improve the uniformity and roundness of the drop pills, the step of screening and regulating might be added.

Example 25

Following materials were taken: 600 g of traditional Chinese medicine composition prepared by Example 1, 5 g of borneol and 3000 g of a mixture of PEG-6000 and PEG-4000 as drop pill matrix.

(1) Melting step: the mixture of PEG-6000 and PEG-4000 was firstly charged into the melting tank and pre-molten by heating to 120° C., into which said pre-mixed traditional Chinese medicine composition was charged to well mix to give the molten medicine liquid;

(2) Dropping step: under pressure the molten medicine liquid was delivered to a dripper that was heated and preserved by steam jacket; at dripper temperature of 80° C. and a vibration frequency of 20 Hz, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −80° C.;

(4) Drying & coating step: resultant solid drop pill was fluidization dried and drug-loading coated to give the coated micro drop pill with the particle size of 0.5 mm~1.0 mm; said drying temperature was 150° C.; and (5) Packaging step: said micro drop pills were loaded into the capsules; 100% of capsules were on-line checkweighed with a capsule checkweigher and packaged to give the final product.

Wherein, during the process of dropping, formation of drop pill was measured visually by using stroboscopic illumination to perform real-time monitoring and adjustment. In order to improve the uniformity and roundness of the drop pills, the step of screening and regulating might be added.

Example 26

Following materials were taken: 600 g of traditional Chinese medicine composition prepared by Example 1, 5 g of borneol and 120 g of PEG-1000 as drop pill matrix.

(1) Melting step: the PEG-1000 was firstly charged into the melting tank and pre-molten by heating to 40° C., into which said pre-mixed traditional Chinese medicine composition was charged to well mix to give the molten medicine liquid;

(2) Dropping step: under pressure the molten medicine liquid was delivered to a dripper that was heated and preserved by steam jacket; at dripper temperature of 40~60° C. and a vibration frequency of 200 Hz, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −100° C.;

(4) Drying & coating step: resultant solid drop pill was fluidization dried and drug-loading coated, fluidized at 20° C., dried at 25° C. for 60 min, at 45° C. for 30 min and at 55° C. for 30 min to give the coated micro drop pill with the particle size of 3.0 mm~4.0 mm; and (5) Packaging step: said micro drop pills were loaded into the capsules; 100% of capsules were on-line checkweighed with a capsule checkweigher and packaged to give the final product.

Wherein, during the process of dropping, formation of drop pill was measured visually by using stroboscopic illumination to perform real-time monitoring and adjustment. In order to improve the uniformity and roundness of the drop pills, the step of screening and regulating might be added.

Example 27

Following materials were taken: 600 g of traditional Chinese medicine composition prepared by Example 1, 5 g of borneol and 3000 g of a mixture of PEG-6000 and PEG-4000 as drop pill matrix.

(1) Melting step: the mixture of PEG-6000 and PEG-4000 was firstly charged into the melting tank and pre-molten by heating to 120° C., into which said pre-mixed traditional Chinese medicine composition was charged and poured into the homogenizer to mix at 1000 rpm for 1 min and melt at 3000 rpm for 1 min, during the melting process, the temperature was kept at 60° C. to obtain the molten medicine liquid;

(2) Dropping step: under pressure the molten medicine liquid was delivered to a dripper that was heated and preserved by steam jacket; at dripper temperature of 70° C., a vibration frequency of 50 Hz and dropping pressure of 0.5 Bar, said molten medicine liquid flowed into the dripper and dropped from the bottom;

(3) Condensation step: the medicine drops were cooled in a cooling duct with low-temperature inert gas to solidify to obtain the solid drop pill; said cooling temperature was 0° C.;

(4) Drying & coating step: resultant solid drop pill was fluidization dried and drug-loading coated to give the coated micro drop pill with the particle size of 0.2 mm; said drying temperature was 150° C.; and (5) Packaging step: said micro drop pills were loaded into the capsules; 100% of capsules were on-line checkweighed with a capsule checkweigher and packaged to give the final product.

Example 28

Following materials were taken: 600 g of traditional Chinese medicine composition prepared by Example 1, 5 g of borneol and 1800 g of PEG-6000 as drop pill matrix.

(1) Melting step: the PEG-6000 was firstly charged into the melting tank and pre-molten by heating to 120° C., into which said pre-mixed traditional Chinese medicine composition was charged and poured into the homogenizer to mix at 5000 rpm for 200 min and melt at 10000 rpm for 1 min, during the melting process, the temperature was kept at 100° C. to obtain the molten medicine liquid;

(2) Dropping step: under pressure the molten medicine liquid was delivered to a dripper that was heated and preserved by steam jacket; at dripper temperature of 300° C., a vibration frequency of 300 Hz and dropping pressure of 4.0 Bar, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −150° C.;

(4) Drying & coating step: resultant solid drop pill was fluidization dried and drug-loading coated to give the coated micro drop pill with the particle size of 4.0 mm; said drying temperature was 150° C.; and (5) Packaging step: said micro drop pills were loaded into the capsules; 100% of capsules were on-line checkweighed with a capsule checkweigher and packaged to give the final product.

Example 29

Following materials were taken: 600 g of traditional Chinese medicine composition prepared by Example 1, 5 g of borneol and 2400 g of PEG-4000 as drop pill matrix.

(1) Melting step: the PEG-4000 was firstly charged into the melting tank and pre-molten by heating to 120° C., into which said pre-mixed traditional Chinese medicine composition was charged, homogenized at 3000 rpm for 10 min and molten homogenizedly at 4000 rpm for 5 min, during the melting process, the temperature was kept at 70~90° C. to obtain the molten medicine liquid;

(2) Dropping step: under pressure the molten medicine liquid was delivered to a dripper that was heated and preserved by steam jacket; at dripper temperature of 70° C., a vibration frequency of 90 Hz and dropping pressure of 1.0 Bar, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −140° C.; and (4) Drying step: resultant solid drop pill was fluidization dried to give the micro drop pill with the particle size of 1.0 mm; said drying temperature was 150° C.

Example 30

Following materials were taken: 600 g of traditional Chinese medicine composition prepared by Example 1, 5 g of borneol and 2400 g of PEG-4000 as drop pill matrix.

(1) Melting step: the PEG-4000 was firstly charged into the melting tank and pre-molten by heating to 120° C., into which said pre-mixed traditional Chinese medicine composition was charged, homogenized at 4000 rpm for 60 min and molten homogenizedly at 9000 rpm for 30 min, during the melting process, the temperature was kept at 90° C. to obtain the molten medicine liquid;

(2) Dropping step: under pressure the molten medicine liquid was delivered to a dripper that was heated and preserved by steam jacket; at dripper temperature of 100° C., a vibration frequency of 200 Hz and dropping pressure of 3.0 Bar, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −140° C.; and (4) Drying step: resultant solid drop pill was fluidization dried to give the micro drop pill with the particle size of 2.0 mm; said drying temperature was 150° C.

Example 31

Following materials were taken: 600 g of traditional Chinese medicine composition prepared by Example 1, 5 g of borneol and 2000 g of PEG-6000 as drop pill matrix.

(1) Melting step: the PEG-6000 was firstly charged into the melting tank and pre-molten by heating to 90° C., into which said pre-mixed traditional Chinese medicine composition was charged to well mix to give the molten medicine liquid;

(2) Dropping step: under pressure the molten medicine liquid was delivered to a dripper that was heated and preserved by steam jacket; at dripper temperature of 80° C. and a vibration frequency of 50 Hz, said molten medicine liquid flowed into the dripper and dropped from the bottom;

(3) Condensation step: the medicine drops were cooled in a cooling duct with low-temperature inert gas to solidify to obtain the solid drop pill; said cooling temperature was −20° C.;

(4) Drying & coating step: resultant solid drop pill was fluidization dried and drug-loading coated give the coated micro drop pill with the particle size of 1.0 mm~2.0 mm; said drying temperature was 75° C.; and (5) Packaging step: said micro drop pills were loaded into the capsules; 100% of capsules were on-line checkweighed with a capsule checkweigher and packaged to give the final product.

Wherein, during the process of dropping, formation of drop pill was measured visually by using stroboscopic illumination to perform real-time monitoring and adjustment. In order to improve the uniformity and roundness of the drop pills, the step of screening and regulating might be added.

As found in the study by the inventors, compared with existing CSDP, the CSMDP prepared by the methods disclosed in the EXAMPLES 15~31 had the merits of good efficacy, high bioavailability, reduced administration dose and good compliance to the patients.

Preparation of Salvianolic Acid T

Example 32

*Salvia Miltiorrhiza* was transferred to an herbal decocting pot, into which 6 times of 0.3% (w/v) sodium bicarbonate aqueous solution based on the amount of *Salvia Miltiorrhiza* was added, decocted for 2.5 h and filtered to give the filtrate. The filtrate was concentrated to obtain the aqueous extract with relative density of 1.22 (80° C.).

The aqueous extract was added with 95% (v/v) ethanol to make the final ethanol content as 60% (v/v) (25° C.) and allowed to stand still for 24 h to give the supernatant. The supernatant was concentrated under reduced pressure to obtain the ethanol-precipitated extract with a relative density of 1.32 (60° C.).

The ethanol-precipitated extract was dissolved with water, passed through AB-8 macroporous resin column and eluted with aqueous hydrochloric acid solution (pH=3.0) until the eluent was nearly colorless. Later, 5 times of 95% (v/v) ethanol based on the column volume was used to elute the column and the eluent was concentrated to give the extract with no smell of alcohol.

The extract obtained from previous step was dissolved with mobile phase (acetonitrile:water:formic acid=15:85:1 by volume) and purified with NOVASEP LC80-600 dynamic axial high-pressure preparative LC. C18 reverse-phase chromatographic column (10 μm, YMC Inc.) was used as stationary phase to carry out the isocratic elution with the mobile phase of acetonitrile:water:formic acid=15:85:1 by volume. The flow rate was at 300 mL/min and detective wavelength at 280 nm. The process of elution was monitored by using HPLC to collect the fraction between 21.2~24.0 min and concentrate to dry with the rotary evaporator to obtain salvianolic acid T.

Afore-obtained salvianolic acid T was dissolved with mobile phase (acetonitrile water:formic acid=17:83:1 by volume) and Waters Prep 400 preparative LC was used to carry out chiral isomer separation. The chromatographic column was CHIRALCEL® OD-RH reverse-phase chiral column (250×20 mm, 5 am) and the mobile phase of acetonitrile:water:formic acid=17:83:1 by volume was used to perform isocratic elution. The flow rate was at 25 mL/min and detective wavelength at 280 nm. The process of elution was monitored by using HPLC to collect the fraction of (S)-salvianolic acid T between retention time of 19.5~21.1 min and (R)-salvianolic acid T between retention time of 23.9~25.3 min. The eluent was concentrated with rotary evaporator at 30° C. and lyophilized to obtain the pure product of (S)- and (R)-salvianolic acid T.

By using a high-resolution mass spectrometry, a quasi-molecular ion peak of (S)-salvianolic acid T was at m/z 537.1033 and (R)-salvianolic acid T at m/z 537.1032.

NMR data assignments for (S)-salvianolic acid T and (R)-salvianolic acid T were seen in the following tables.

TABLE 6

$^1$H (DMSO, J Hz) data assignment for the (R)-salvianolic acid T

| No. | $\delta_H$ | $\delta c$ | $^1$H-$^1$H COSY | HMBC |
|---|---|---|---|---|
| 1 | — | 123.7 | | H-5, H-8 |
| 2 | — | 126.4 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.31 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 113.9 | H-7 | H-7 |
| 9 | — | 166.0 | | H-7, H-8, H-8' |
| 1' | — | 127.1 | | H-2', H-5', H-8', H-7' |
| 2' | 6.62 (1H, s) | 116.5 | H-6' | H-6' |
| 3' | — | 143.9 | | H-2', H-5' |
| 4' | — | 144.8 | | H-2', H-5', H-6' |
| 5' | 6.63 (1H, d, 8.0 Hz) | 115.5 | H-6' | H-6' |
| 6' | 6.47 (1H, d, 8.0 Hz) | 120.0 | H-2', 5' | H-2', H-5' |
| 7' | 2.89 (2H, ddd, 14.0, 8.0, 4.5 Hz) | 36.0 | H-8' | H-2', H-5', H-6', H-8' |
| 8' | 4.93 (1H, dd, 8.0, 4.5 Hz) | 72.8 | H-7' | H-7' |
| 9' | — | 170.6 | | H-7', H-8' |
| 1" | — | 126.0 | | H-2" |
| 2" | 6.44 (1H, d, 2.0 Hz) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 8.5 Hz) | 115.3 | H-6" | |
| 6" | 6.43 (1H, dd, 8.5, 2.0 Hz) | 122.9 | H-2", 5" | H-2", H-7" |
| 7" | 7.69 (1H, s) | 141.1 | | H-6" |
| 8" | — | 123.4 | | H-7" |
| 9" | — | 168.4 | | H-7" |

TABLE 7

$^1$H (DMSO, J Hz) data assignment for the (S)-salvianolic acid T

| No. | $\delta_H$ | $\delta c$ | $^1$H-$^1$H COSY | HMBC |
|---|---|---|---|---|
| 1 | — | 123.8 | | H-5, H-8 |
| 2 | — | 126.3 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.29 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 114.0 | H-7 | H-7 |
| 9 | — | 165.9 | | H-7, H-8, H-8' |
| 1' | — | 127.2 | | H-2', H-5', H-8', H-7' |
| 2' | 6.62 (1H, s) | 116.5 | H-6' | H-6', H-7' |
| 3' | — | 143.9 | | H-2', H-5', H-6' |
| 4' | — | 144.9 | | H-2', H-5' |
| 5' | 6.63 (1H, d, 8.0 Hz) | 115.5 | H-6' | |
| 6' | 6.45 (1H, d, 8.0 Hz) | 120.1 | H-2', 5' | H-2', H-5', H-7' |
| 7' | 2.87 (2H, ddd, 14.0, 8.0, 4.0 Hz) | 36.1 | H-8' | H-2', H-5', H-6', H-8' |
| 8' | 4.92 (1H, dd, 8.0, 4.0 Hz) | 72.9 | H-7' | H-7' |
| 9' | — | 170.6 | | H-7', H-8' |
| 1" | — | 126.0 | | H-5" |
| 2" | 6.43 (1H, d, 2.0 Hz) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 9.0 Hz) | 115.3 | H-6" | |
| 6" | 6.43 (1H, dd, 8.5, 2.0 Hz) | 122.9 | H-2", 5" | H-2", H-7" |
| 7" | 7.69 (1H, s) | 141.1 | | H-2", H-6" |
| 8" | — | 123.3 | | |
| 9" | — | 168.4 | | H-7" |

In order to better prove the merits of the present invention, the trial was presented as follows:

Trial Example 1

1. Materials 1.1 Animals:

SD male rats, weighing 200 g, were purchased from Beijing Weitonglihua Experimental Animal Co., Ltd, with certification No.: SCXK (JING) 2007-0001.

Rabbits, male, weighing 1.7~2.0 kg, were purchased from Qinglongshan Animal Reproduction Plant, Jiangning Country, Nanjing with certification No.: SCXK (SU) 2007-2008.

1.2 Drugs and Reagents

The *Salvia Miltiorrhiza* and *Panax Notoginseng* extracts were divided into two types, which were prepared by the method of Example 1, Extract A (with borneol) and Extract B (without borneol). Chloral hydrate and triphenyl tetrazolium chloride (TTC) were used.

Aspirin enteric-coated tablet was purchased from Baijingyu Pharmaceutical Inc, Nangjing. Batch number was 111001.

Arachidonic acid (AA) was provided by Sigma Inc in specification of 10 mg/bottle, and batch number was 1001126252.

Monosodium adenosine diphosphate (ADP) was provided by Shanghai Boao Bio-tech Inc (Imported). Batch number was 990527.

Collagen was provided by Sigma Inc in specification of 10 mg/bottle, and batch number was 1001162038.

2. Protocol 2.1 Acute Myocardial Infarction Experiment in Rats 32 rats were randomly divided into groups according to the body weight: the blank group, model group, group A (with borneol) and group B (without borneol); 8 rats in each group.

After grouping, all animals were administrated intragastrically for 1 week, which was seen in Table 8. On $8^{th}$ day, the animals were anesthetized by intraperitoneal injection of 10% chloral hydrate (3 ml/kg) and fixed on a small plate in a supine position. Conductors were inserted under the skin of right forelimb and both hind limbs, which was connected with the MedLab-U/8c bio-signal collecting-processing system to record the ECG of rats. Hair on front wall of left chest was clipped. Oral tracheal cannula was performed and the animal respirator was connected at respiratory frequency of 80 breaths/min, tidal volume 3 ml/100 g and I:E=1:2. Chest on left front chest lateral side was incised to cut $3^{rd}$ rib and the pericardium carefully lifted with forceps to tear apart. Left coronary vein trunk pass between the lower edge of left atrial appendage and pulmonary artery cone was observed in most of animals, accompanied with LAD. Medical suture (4-0) was used to ligate LAD and a small amount of myocardial tissue 1~2 mm from the low edge of left atrial appendage inside the interventricular sulcus in the vicinity of left coronary vein trunk. Chest was closed layer by layer. The tracheal tube was detubated until the respiration was recovered in rats.

Testing index: after 4 h ligation, the animals were euthanized. The hearts were taken out and washed with 0.9% sodium chloride injection to absorb the water. Along the coronary sulcus, the atrium was cut to weigh wet ventricular mass. The heart was sliced into 1 mm thickness of myocardial sections in parallel from the apex to the base portion along ventricular ditch. Obtained myocardium was placed in TTC colorant to dye for 15 min on 37° C. thermal water bath. Normal myocardium was dyed red and infarcted area white. Wet mass in each section of infarcted area was weighed to calculate the myocardial infarction rate (MIR).

TABLE 8 grouping and administrating

| Groups | dosage | Dose | Administration time |
| --- | --- | --- | --- |
| Sham operation | | 1 ml/100 g | 7 d |
| Model group | | 1 ml/100 g | 7 d |
| Group A | 83.7 mg/kg | 1 ml/100 g | 7 d |
| Group B | 83.7 mg/kg | 1 ml/100 g | 7 d |

2.2 Platelet Aggregation Rate Trial in Rabbits

The rabbits were randomly grouped into 4 groups: the model group was given with distilled water, the aspirin group (60 mg/ml), Extract A groups of low dose and high dose at 42 and 84 mg/kg (respectively 1~2 times of clinic equivalent dosage), intragastrically administrated, once a day for 7 consecutive days. The volume of medicine administrated was 1 ml/kg body weight. 60 min after intragastric administration on $7^{th}$ day, the animals were anesthetized locally, blooded through carotid artery, anticoagulated with sodium citrate (3.8%) 1:9 and centrifugated at 1000 r/min for 10 min. Platelet-rich plasma (PRP) was taken and the remain centrifugated at 3000 r/min to take platelet-poor plasma (PPP. Aggregation was induced by ADP (final concentration 3 μg/ml), AA (final concentration 80 μg/ml) and collagen (5 μg/ml). STEELIEX platelet aggregation & coagulation factor analyzer was used to measure the maximum platelet aggregation rate and to calculate inhibition rate according to following formula.

$$\text{Platelet aggregation inhibiting rate (\%)} = \frac{\text{Platelet aggregation rate in model group} - \text{Platelet aggregation rate in treatment group}}{\text{Platelet aggregation rate in model group}} \times 100$$

3. Results 3.1 Experimental Results of Myocardial Infarction in Rats

The results were in Table 9. 7 days after pre-administration, compared with the model group (0.1209±0.0199 g), the weights of myocardial infarction in group A and group B (0.0685±0.0182 g, 0.0923±0.0191 g) were decreased obviously, having statistical significance. According to the results of inter-group comparison, the ratio of myocardial infarction in group A was much less than that in group B, having significant difference between two groups (p<0.05).

TABLE 9 effect of *Salvia Militiorrhiza* and *Panax Notoginseng* extract on weight of myocardial infarction in rabbits (n = 6)

| Group | Dose (mg/kg) | Average wet weight of whole heart (g) | Average wet weight of myocardial infarction (g) | Wet weight of infarction/ wet weight of whole heart × 100% (%) |
| --- | --- | --- | --- | --- |
| Blank group | | 0.887 ± 0.044 | 0 | 0.00 ± 0.00 |
| Model group | | 0.926 ± 0.094 | 0.121 ± 0.020 | 13.03 ± 1.61 |
| Group A | 83.7 | 0.872 ± 0.046 | 0.069 ± 0.018* | 7.91 ± 2.21* |
| Group B | 83.7 | 0.925 ± 0.127 | 0.092 ± 0.019*# | 10.04 ± 1.87*# |

Note:
compared with the model group,
*p < 0.05; compared with Group A,
p < 0.05

3.2 Effect on Platelet Aggregation Rate in Rabbits

As shown in Table 10, Extract A was proven to have inhibitory effect on ADP-induced platelet aggregation in rabbits, which, compared with the blank group, had a significant difference. Compared with the aspirin group, no significant difference was found in the group A in inhibiting ADP-induced platelet aggregation.

TABLE 10 effect of Extract A on ADP-induced platelet aggregation in rabbits ($\bar{x} \pm s$, n = 8)

| Group | Dose (mg/kg) | Platelet aggregation rate (%) |
|---|---|---|
| Blank group | 0 | 30.58 ± 5.35 |
| Aspirin group | 60 | 19.15 ± 4.08** |
| Group A-low dose | 42 | 24.33 ± 5.21* |
| Group A-high dose | 84 | 20.69 ± 3.47** |

*$P < 0.05$,
**$P < 0.01$, compared with the blank group.

As shown in Table 11, Extract A was proven to have inhibitory effect on AA-induced platelet aggregation in rabbits, which, compared with the blank group, had a significant difference. Compared with the aspirin group, no significant difference was found in the group A in inhibiting AA-induced platelet aggregation.

TABLE 11 effect of Extract A on AA-induced platelet aggregation in rabbits ($\bar{x} \pm s$, n = 8)

| Group | Dose (mg/kg) | Platelet aggregation rate (%) |
|---|---|---|
| Blank group | 0 | 9.8 ± 2.33 |
| Aspirin group | 60 | 5.80 ± 1.85** |
| Group A-low dose | 42 | 7.91 ± 3.12 |
| Group A-high dose | 84 | 5.95 ± 1.54** |

*$P < 0.05$,
**$P < 0.01$, compared with the model group.

As shown in Table 12, Extract A was proven to have inhibitory effect on collagen-induced platelet aggregation in rabbits, which, compared with the blank group, had a significant difference. Compared with the aspirin group, no significant difference was found in the group A in inhibiting collagen-induced platelet aggregation.

TABLE 12 effect of Extract A on collegan-induced platelet aggregation in rabbits ($\bar{x} \pm s$, n = 8)

| Group | Dose (mg/kg) | Platelet aggregation rate (%) |
|---|---|---|
| Blank group | 0 | 16.6 ± 4.92 |
| Aspirin group | 60 | 6.06 ± 2.07** |
| Group A-low dose | 42 | 10.21 ± 3.54* |
| Group A-high dose | 84 | 5.78 ± 0.98** |

*$P < 0.05$,
**$P < 0.01$, compared with the model group.

4. Discussion

As shown in the results, administration of *Salvia Miltiorrhiza* and *Panax Notoginseng* extract for 7 consecutive days could take effect of antimyocardial infarction in ligated rats.

In Group A, the *Salvia Miltiorrhiza* and *Panax Notoginseng* extract with borneol was administrated for 7 consecutive days. Obviously, the myocardial infarction rate was less than that in Group B (without borneol) and had significantly inhibitory effect on ADP, AA or collagen induced platelet aggregation in rabbits.

The preliminary conclusion showed that addition of borneol might strengthen the efficacy of anti-myocardial infarction.

Trial Example 2: Comparative Study on Effect of Acute Myocardial Infarction in Rats Between Two Kinds of CSDPs 1. Animals:

SD male rats, weighing 340~360 g, were purchased from Beijing Weitonglihua Experimental Animal Co., Ltd, with certification No.: SCXK (JING) 2007-0001.

2. Drugs, Reagents and Apparatus

CSMDP was prepared by the method of Preparative Example 15 of CSMDP.

CSDP, used as compared drug, was commercially available in China, prepared by Tianjin Tasly Pharmaceutical Co., Ltd.

Anesthesia was performed by chloral hydrate and triphenyl tetrazolium chloride (TTC).

Apparatus: MedLab-U/8c bio-signal collecting-processing system, purchased from Nanjin Meiyi Inc.

3. Protocol

Grouping: rats were randomly divided into groups according to the body weight: S group (the sham operation group), M group (the model group), Y group (the positive group, Metoprolol Tartrate, Lot No. 1201039), F group (the CSMDP group in the present invention) and G group (the CSDP group commercially available in China, batch number: 2011L16); 10 rats in each group.

Modeling and Administrating Method:

After grouping, the animals were administrated intragastrically for 7 days, which was seen in Table 13. On $8^{th}$ day, the rats were anesthetized by intraperitoneal injection of 10% chloral hydrate (3 ml/kg) and fixed on a small wood plate in a supine position. Pins were inserted under the skin of right forelimb and both hind limbs, which was connected with the MedLab-U/8c bio-signal collecting-processing system to record the ECG of rats. Hair on front wall of left chest was clipped. Oral tracheal cannula was performed and the animal respirator was connected at respiratory frequency of 80 breaths/min, tidal volume 3 ml/100 g and I:E=1:2. Chest on left front chest lateral side was incised to cut $3^{rd}$ rib and the pericardium carefully lifted with forceps to tear apart. Left coronary vein trunk pass between the lower edge of left atrial appendage and pulmonary artery cone was observed in most of animals, accompanied with LAD. Medical suture (4-0) was used to ligate LAD and a small amount of myocardial tissue 1~2 mm from the low edge of left atrial appendage inside the interventricular sulcus in the vicinity of left coronary vein trunk. The rats with elevated J point by 0.1 mV in ECG and pale LVAW (left ventricular anterior wall) represented the successful modeling. Chest was closed layer by layer. The tracheal tube was detubated until the respiration was recovered in rats. ECG was recorded continuously for 4 hours. Rats were anesthetized, heart taken out, sliced and dyed to calculate myocardial infarction rate (MIR). The serum was for later use.

MIR (%)=wet weight of infarction area/wet weight of whole heart×100%

TABLE 13

Grouping and administration

| Group | Concentrate (mg/kg) | Dose | Pre-administration time |
|---|---|---|---|
| S group | 110 | 1 ml/100 g | 7 d |
| M group | 223 | 1 ml/100 g | 7 d |
| Y group | 4.5 | 1 ml/100 g | 7 d |
| G group | 115 | 1 ml/100 g | 7 d |
| F group | 84 | 1 ml/100 g | 7 d |

4. Results 4.1 Effect on MIR

The results were in Table 14. As shown in Table 14, 7 days after pre-administration, MIR in M group was significantly higher than that in S group, suggesting the successful modeling. MIR in G group and F group were respectively 3.38% and 3.32%, significantly lower than that in M group (5.07%), having a significant difference ($p<0.01$). It was indicated that both samples had a certain effect against acute myocaudial infarction. However, there was no significantly statistical difference ($p>0.05$) in comparison to those in G group and F group.

TABLE 14 effect of CSDP in each group on MIR

| Group | N | Average wet weight of whole heart (g) | Average wet weight of infarction area (g) | MIR (%) |
|---|---|---|---|---|
| S group | 8 | 0.8254 ± 0.0294 | 0.0000 ± 0.0000 | 0.00 ± 0.00 |
| M group | 10 | 0.8207 ± 0.0447 | 0.0414 ± 0.0051 | 5.07 ± 0.75 |
| Y group | 9 | 0.8783 ± 0.0571 | 0.0233 ± 0.0038 | 2.65 ± 0.33* |
| G group | 10 | 0.8493 ± 0.0641 | 0.0288 ± 0.0052 | 3.38 ± 0.49*# |
| F group | 10 | 0.8061 ± 0.0668 | 0.0268 ± 0.0054 | 3.32 ± 0.59*# |

Note:
compared with the M group,
*$p < 0.01$; compared with the Y group,
$p < 0.01$ 4.2 Effect on Heart Rate in Rats with Myocardial Infarction As shown in Table 15, the descending order of heart rate in each group was F group, G group, M group, Y group and S group within observation time and 0~1 hour after ligation. 1 hour later, the heart rate in each group was decreased. Within observation time, the variation of heart rate in Y group and S group was relatively stable. There was no significant difference on heart rate in rats among groups.

TABLE 15 effect of CSDP in each group on heart rate (beat/min)

| Group | N | 0 s | 5 s | 10 s | 5 min | 10 min | 30 min | 1 h | 2 h | 3 h | 4 h |
|---|---|---|---|---|---|---|---|---|---|---|---|
| S group | 8 | 390 ± 50 | 390 ± 52 | 400 ± 51 | 407 ± 43 | 401 ± 57 | 386 ± 69 | 394 ± 58 | 417 ± 44 | 364 ± 42 | 358 ± 36 |
| M group | 10 | 416 ± 83 | 447 ± 72 | 436 ± 67 | 444 ± 43 | 423 ± 39 | 423 ± 32 | 399 ± 31 | 361 ± 45 | 363 ± 46 | 336 ± 59 |
| Y group | 9 | 377 ± 48 | 423 ± 39 | 419 ± 41 | 424 ± 29 | 431 ± 17 | 413 ± 34 | 421 ± 47 | 416 ± 33 | 380 ± 66 | 395 ± 52 |
| G group | 10 | 431 ± 43 | 452 ± 27 | 444 ± 24 | 445 ± 29 | 424 ± 27 | 422 ± 25 | 397 ± 25 | 392 ± 40 | 347 ± 39 | 331 ± 38 |
| F group | 10 | 449 ± 28 | 498 ± 7 | 468 ± 34 | 474 ± 35 | 466 ± 34 | 426 ± 40 | 412 ± 40 | 388 ± 51 | 377 ± 60 | 365 ± 56 |

5. Conclusion

At dose of this study, the medicines in each group were proven to have a certain effect against myocardial infarction in ligature rats on coronary artery; especially the CSMDP of the present invention (84 mg/kg) had MIR of 3.38±0.49%, having a similar efficacy of MIR (3.32±0.59%) with the commercially available CSDP (115 mg/kg). Obviously, the CSMDP at a dose of 84 mg/kg reached the same effect with the commercially available CSDP at 115 mg/kg. The CSMDP had a better efficacy than the commercially available CSDP, having the merits of high bioavailability, reduced administration dose and good compliance to the patients.

What is claimed is:

1. A Chinese medicine composition consisting of the following materials by weight percentage: 50.0%~99.9% of *Salvia Miltiorrhiza* and *Panax Notoginseng* extract and 0.1%~50.0% of borneol, wherein the *Salvia Miltiorrhiza* and *Panax Notoginseng* extract comprises the following ingredients by weight percentage:
Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(2~6):(0.5~2): (1~3):(0.2~1):(0.2~1):(0.5~2):(0.5~2):(0.2~1):(1~4): (0.1~0.5):(1~4):(0.1~1):(0.01~0.05):(0.05~0.1): (0.02~0.1):(0.1~0.5).

2. The Chinese medicine composition according to claim 1, wherein said Chinese medicine composition consists of the following materials by weight percentage: 75.0%~99.9% of *Salvia Miltiorrhiza* and *Panax Notoginseng* extract and 0.1%~25.0% of borneol.

3. The Chinese medicine composition according to claim 1, wherein said traditional Chinese medicine composition is composed of the following materials by weight percentage: 90.0%~99.9% of *Salvia Miltiorrhiza* and *Panax Notoginseng* extract and 0.1%~10.0% of borneol.

4. The Chinese medicine composition according to claim 1, wherein the *Salvia Miltiorrhiza* and *Panax Notoginseng* extract comprises the following ingredients by weight parts:
Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=(3~4):(0.9~1.2): (1.4~2.0):(0.5~0.7):(0.5~0.9):(1~1.6):(0.7~1.2): (0.5~0.9):(1.8~2.8):(0.2~0.4):(1.7~2.2):(0.2~0.6): (0.03~0.04):(0.07~0.08):(0.05~0.06):(0.26~0.28).

5. The Chinese medicine composition according to claim 4, wherein the *Salvia Miltiorrhiza* and *Panax Notoginseng* extract comprises the following ingredients by weight parts:
Danshensu:Salvianolic acid T:protocatechuic aldehyde: Salvianolic acid D:rosmarinic acid:Salvianolic acid B:Salvianolic acid A:*Panax Notoginseng* Saponin R1:Ginsenoside Rg1:Ginsenoside Re:Ginsenoside Rb1:Ginsenoside Rd:dihydrotanshinone I:tanshinone I:cryptotanshinone:tanshinone IIA=3.6:1.1:1.7:0.6:0.7: 1.3:0.9:0.7:2.4:0.3:1.8:0.4:0.03:0.07:0.06:0.27.

6. The Chinese medicine composition according to claim 1, wherein the *Salvia Miltiorrhiza* and *Panax Notoginseng* extract is prepared with the following crude medicine by weight parts: *Salvia Miltiorrhiza* 75~90 parts and *Panax Notoginseng* 10~25 parts.

7. The Chinese medicine composition according to claim 6, wherein the *Salvia Miltiorrhiza* and *Panax Notoginseng* extract is prepared with the following crude medicine by weight parts: *Salvia Miltiorrhiza* 82~84 parts, *Panax Notoginseng* 16~17 parts.

8. A pharmaceutical preparation comprising the Chinese medicine composition according to claim 1 and pharmaceutically acceptable carriers.

9. The pharmaceutical preparation according to claim 8, wherein said pharmaceutical preparation is in a dosage form of drop pill or micro drop pill, wherein said micro drop pill is prepared with the Chinese medicine composition and drop pill matrix in a ratio of 1:5~5:1 by weight.

10. The pharmaceutical preparation according to claim 9, wherein said pharmaceutical preparation is a compound *Salvia* micro drop pill.

* * * * *